United States Patent
Gunasekaran et al.

(10) Patent No.: US 12,082,917 B2
(45) Date of Patent: Sep. 10, 2024

(54) SYSTEMS, DEVICES, AND METHODS FOR ASSESSING EFFICACY OF RENAL NEUROMODULATION THERAPY

(71) Applicant: Medtronic Ireland Manufacturing Unlimited Company, Dublin (IE)

(72) Inventors: Venmathi Gunasekaran, Santa Rosa, CA (US); Douglas Hettrick, Andover, MN (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 506 days.

(21) Appl. No.: 15/960,333

(22) Filed: Apr. 23, 2018

(65) Prior Publication Data
US 2019/0223754 A1    Jul. 25, 2019

Related U.S. Application Data

(60) Provisional application No. 62/621,304, filed on Jan. 24, 2018.

(51) Int. Cl.
*A61B 5/107*    (2006.01)
*A61B 5/00*    (2006.01)
(Continued)

(52) U.S. Cl.
CPC ........ *A61B 5/0538* (2013.01); *A61B 5/02007* (2013.01); *A61B 5/0535* (2013.01);
(Continued)

(58) Field of Classification Search
CPC ...... A61B 18/1492; A61B 2018/00404; A61B 2018/00434; A61B 2018/00577; A61B 2018/00875; A61B 5/0538
See application file for complete search history.

(56) References Cited

U.S. PATENT DOCUMENTS

| | | |
|---|---|---|
| 4,602,624 A | 7/1986 | Naples et al. |
| 4,649,936 A | 3/1987 | Ungar et al. |

(Continued)

FOREIGN PATENT DOCUMENTS

| | | |
|---|---|---|
| EP | 0768841 A1 | 4/1997 |
| EP | 1169976 A1 | 1/2002 |

(Continued)

OTHER PUBLICATIONS

Allen, E.V., Sympathectomy for essential hypertension, Circulation, 1952, 6:131-140.

(Continued)

*Primary Examiner* — Khadijeh A Vahdat
*Assistant Examiner* — Yasamin Ekrami
(74) *Attorney, Agent, or Firm* — Shumaker & Sieffert, P.A

(57) ABSTRACT

Systems and methods for performing, assessing, and adjusting neuromodulation therapy are disclosed herein. One method for assessing the likely efficacy of neuromodulation therapy includes positioning a neuromodulation catheter at a target site within a renal blood vessel of a human patient and obtaining a measurement related to a diameter of the renal blood vessel via the neuromodulation catheter. The method can further include determining a diameter of the renal blood vessel at or near the target site based on the measurement. In some embodiments, (i) one or more parameters of neuromodulation energy to be delivered to the renal blood vessel can be adjusted based on the determined diameter and/or (ii) the neuromodulation catheter may be repositioned within the renal blood vessel.

22 Claims, 12 Drawing Sheets

(51) Int. Cl.
  *A61B 5/02* (2006.01)
  *A61B 5/0535* (2021.01)
  *A61B 5/0538* (2021.01)
  *A61B 18/14* (2006.01)
  *A61B 18/00* (2006.01)
  *A61B 90/00* (2016.01)

(52) U.S. Cl.
  CPC .......... *A61B 5/1076* (2013.01); *A61B 5/4035* (2013.01); *A61B 5/4848* (2013.01); *A61B 5/6857* (2013.01); *A61B 18/1492* (2013.01); *A61B 5/6853* (2013.01); *A61B 2018/00214* (2013.01); *A61B 2018/00404* (2013.01); *A61B 2018/00434* (2013.01); *A61B 2018/00511* (2013.01); *A61B 2018/00577* (2013.01); *A61B 2018/00702* (2013.01); *A61B 2018/00761* (2013.01); *A61B 2018/00875* (2013.01); *A61B 2018/1435* (2013.01); *A61B 2090/061* (2016.02); *A61B 2505/05* (2013.01); *A61B 2562/0209* (2013.01)

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,228,442 A | 7/1993 | Imran |
| 5,300,068 A | 4/1994 | Rosar et al. |
| 5,301,683 A | 4/1994 | Durkan |
| 5,358,514 A | 10/1994 | Schulman et al. |
| 5,368,591 A | 11/1994 | Lennox et al. |
| 5,423,744 A | 6/1995 | Gencheff et al. |
| 5,423,808 A | 6/1995 | Edwards et al. |
| 5,423,810 A | 6/1995 | Goble et al. |
| 5,425,364 A | 6/1995 | Imran |
| 5,437,662 A | 8/1995 | Nardella |
| 5,437,664 A | 8/1995 | Cohen et al. |
| 5,472,443 A | 12/1995 | Cordis et al. |
| 5,484,400 A | 1/1996 | Edwards et al. |
| 5,496,312 A | 3/1996 | Klicek |
| 5,540,681 A | 7/1996 | Strul et al. |
| 5,540,684 A | 7/1996 | Hassler, Jr. |
| 5,562,721 A | 10/1996 | Marchlinski et al. |
| 5,571,147 A | 11/1996 | Sluijter et al. |
| 5,573,533 A | 11/1996 | Strul |
| 5,584,830 A | 12/1996 | Ladd et al. |
| 5,588,964 A | 12/1996 | Imran et al. |
| 5,599,345 A | 2/1997 | Edwards et al. |
| 5,626,576 A | 5/1997 | Janssen |
| 5,658,619 A | 8/1997 | Kirschner et al. |
| 5,672,174 A | 9/1997 | Gough et al. |
| 5,688,266 A | 11/1997 | Edwards et al. |
| 5,697,882 A | 12/1997 | Eggers et al. |
| 5,697,925 A | 12/1997 | Taylor |
| 5,700,282 A | 12/1997 | Zabara |
| 5,702,386 A | 12/1997 | Stern et al. |
| 5,707,400 A | 1/1998 | Terry, Jr. et al. |
| 5,735,846 A | 4/1998 | Panescu et al. |
| 5,755,715 A | 5/1998 | Stern et al. |
| 5,766,151 A | 6/1998 | Valley et al. |
| 5,769,847 A | 6/1998 | Panescu et al. |
| 5,772,590 A | 6/1998 | Webster, Jr. |
| 5,810,802 A | 9/1998 | Panescu et al. |
| 5,817,092 A | 10/1998 | Behl |
| 5,817,093 A | 10/1998 | Williamson, IV et al. |
| 5,859,762 A | 1/1999 | Clark et al. |
| 5,860,974 A | 1/1999 | Abele |
| 5,865,787 A | 2/1999 | Shapland |
| 5,868,737 A | 2/1999 | Taylor et al. |
| 5,871,481 A | 2/1999 | Kannenberg et al. |
| 5,893,885 A | 4/1999 | Webster et al. |
| 5,906,614 A | 5/1999 | Stern et al. |
| 5,907,589 A | 5/1999 | Koifman et al. |
| 5,944,710 A | 8/1999 | Dev et al. |
| 5,954,719 A | 9/1999 | Chen et al. |
| 5,976,128 A | 11/1999 | Schilling et al. |
| 5,983,141 A | 11/1999 | Sluijter et al. |
| 6,004,269 A | 12/1999 | Crowley et al. |
| 6,009,877 A | 1/2000 | Edwards |
| 6,023,638 A | 2/2000 | Swanson |
| 6,039,731 A | 3/2000 | Taylor et al. |
| 6,066,134 A | 5/2000 | Eggers et al. |
| 6,080,149 A | 6/2000 | Huang et al. |
| 6,099,524 A | 8/2000 | Lipson et al. |
| 6,113,592 A | 9/2000 | Taylor |
| 6,117,101 A | 9/2000 | Diederich et al. |
| 6,123,702 A | 9/2000 | Swanson et al. |
| 6,123,703 A | 9/2000 | Tu et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,183,417 B1 | 2/2001 | Geheb et al. |
| 6,183,468 B1 | 2/2001 | Swanson et al. |
| 6,197,021 B1 | 3/2001 | Panescu et al. |
| 6,210,403 B1 | 4/2001 | Klicek |
| 6,212,426 B1 | 4/2001 | Swanson |
| 6,217,573 B1 | 4/2001 | Webster |
| 6,219,577 B1 | 4/2001 | Brown, III et al. |
| 6,224,592 B1 | 5/2001 | Eggers et al. |
| 6,238,387 B1 | 5/2001 | Miller, III |
| 6,245,065 B1 | 6/2001 | Panescu et al. |
| 6,246,912 B1 | 6/2001 | Sluijter et al. |
| 6,262,695 B1 | 7/2001 | McGowan |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,293,941 B1 | 9/2001 | Strul et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,358,246 B1 | 3/2002 | Behl et al. |
| 6,405,732 B1 | 6/2002 | Edwards et al. |
| 6,413,255 B1 | 7/2002 | Stern |
| 6,423,057 B1 | 7/2002 | He et al. |
| 6,428,537 B1 | 8/2002 | Swanson et al. |
| 6,451,015 B1 | 9/2002 | Rittman, III et al. |
| 6,464,696 B1 | 10/2002 | Oyama et al. |
| 6,488,678 B2 | 12/2002 | Sherman |
| 6,488,679 B1 | 12/2002 | Swanson et al. |
| 6,494,880 B1 | 12/2002 | Swanson et al. |
| 6,500,172 B1 | 12/2002 | Panescu et al. |
| 6,506,189 B1 | 1/2003 | Rittman et al. |
| 6,508,815 B1 | 1/2003 | Strul et al. |
| 6,511,476 B2 | 1/2003 | Hareyama |
| 6,514,226 B1 | 2/2003 | Levin et al. |
| 6,514,248 B1 | 2/2003 | Eggers et al. |
| 6,522,926 B1 | 2/2003 | Kieval et al. |
| 6,542,781 B1 | 4/2003 | Koblish et al. |
| 6,558,378 B2 | 5/2003 | Sherman et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,635,057 B2 | 10/2003 | Harano et al. |
| 6,640,120 B1 | 10/2003 | Swanson et al. |
| 6,648,883 B2 | 11/2003 | Francischelli et al. |
| 6,666,862 B2 | 12/2003 | Jain et al. |
| 6,679,269 B2 | 1/2004 | Swanson |
| 6,682,527 B2 | 1/2004 | Strul |
| 6,685,648 B2 | 2/2004 | Flaherty et al. |
| 6,685,700 B2 | 2/2004 | Behl et al. |
| 6,711,444 B2 | 3/2004 | Koblish |
| 6,730,079 B2 | 5/2004 | Lovewell |
| 6,733,498 B2 | 5/2004 | Paton et al. |
| 6,736,835 B2 | 5/2004 | Pellegrino et al. |
| 6,752,804 B2 | 6/2004 | Simpson et al. |
| 6,761,716 B2 | 7/2004 | Kadhiresan et al. |
| 6,845,267 B2 | 1/2005 | Harrison et al. |
| 6,849,073 B2 | 2/2005 | Hoey et al. |

(56) References Cited

U.S. PATENT DOCUMENTS

| | | |
|---|---|---|
| 6,850,801 B2 | 2/2005 | Kieval et al. |
| 6,855,141 B2 | 2/2005 | Lovewell |
| 6,855,142 B2 | 2/2005 | Harano et al. |
| 6,885,888 B2 | 4/2005 | Rezai |
| 6,893,436 B2 | 5/2005 | Woodard et al. |
| 6,917,834 B2 | 7/2005 | Koblish et al. |
| 6,923,808 B2 | 8/2005 | Taimisto |
| 6,936,047 B2 | 8/2005 | Nasab et al. |
| 6,939,346 B2 | 9/2005 | Kannenberg et al. |
| 6,949,097 B2 | 9/2005 | Stewart et al. |
| 6,955,675 B2 | 10/2005 | Jain |
| 6,989,010 B2 | 1/2006 | Francischelli et al. |
| 7,001,379 B2 | 2/2006 | Behl et al. |
| 7,001,381 B2 | 2/2006 | Harano et al. |
| 7,008,417 B2 | 3/2006 | Eick |
| 7,025,764 B2 | 4/2006 | Paton et al. |
| 7,029,470 B2 | 4/2006 | Francischelli et al. |
| 7,066,933 B2 | 6/2006 | Hagg |
| 7,076,399 B2 | 7/2006 | Godara |
| 7,104,985 B2 | 9/2006 | Martinelli |
| 7,108,694 B2 | 9/2006 | Miura et al. |
| 7,131,445 B2 | 11/2006 | Amoah |
| 7,149,574 B2 | 12/2006 | Yun et al. |
| 7,160,296 B2 | 1/2007 | Pearson et al. |
| 7,162,303 B2 | 1/2007 | Levin et al. |
| 7,169,144 B2 | 1/2007 | Hoey et al. |
| 7,221,979 B2 | 5/2007 | Zhou et al. |
| 7,226,447 B2 | 6/2007 | Uchida et al. |
| 7,247,155 B2 | 7/2007 | Hoey et al. |
| 7,250,048 B2 | 7/2007 | Francischelli et al. |
| 7,258,688 B1 | 8/2007 | Shah et al. |
| 7,364,578 B2 | 4/2008 | Francischelli et al. |
| 7,381,200 B2 | 6/2008 | Katoh et al. |
| 7,390,894 B2 | 6/2008 | Weinshilboum et al. |
| 7,367,972 B2 | 9/2008 | Francischelli et al. |
| 7,429,261 B2 | 9/2008 | Kunis et al. |
| 7,533,002 B2 | 5/2009 | Godara |
| 7,582,084 B2 | 9/2009 | Swanson et al. |
| 7,596,469 B2 | 9/2009 | Godara |
| 7,617,005 B2 | 11/2009 | Demarais et al. |
| 7,647,115 B2 | 1/2010 | Levin et al. |
| 7,651,492 B2 | 1/2010 | Wham |
| 7,653,438 B2 | 1/2010 | Deem et al. |
| 7,717,909 B2 | 5/2010 | Strul et al. |
| 7,717,948 B2 | 5/2010 | Demarais et al. |
| 7,778,703 B2 | 8/2010 | Gross et al. |
| 7,792,589 B2 | 9/2010 | Levy, Jr. et al. |
| 7,799,020 B2 | 9/2010 | Shores et al. |
| 7,824,399 B2 | 11/2010 | Francischelli et al. |
| 7,837,679 B2 | 11/2010 | Biggs et al. |
| 7,842,076 B2 | 11/2010 | Zikorus et al. |
| 7,846,160 B2 | 12/2010 | Payne et al. |
| 7,853,333 B2 | 12/2010 | Demarais |
| 7,887,534 B2 | 2/2011 | Hamel et al. |
| 7,901,400 B2 | 3/2011 | Wham et al. |
| 7,922,714 B2 | 4/2011 | Stevens-Wright |
| 7,927,328 B2 | 4/2011 | Orszulak et al. |
| 7,959,626 B2 | 6/2011 | Hong et al. |
| 7,963,962 B2 | 6/2011 | Thompson et al. |
| 7,972,328 B2 | 7/2011 | Wham et al. |
| 7,976,540 B2 | 7/2011 | Daw et al. |
| 8,048,070 B2 | 11/2011 | O'Brien et al. |
| 8,058,771 B2 | 11/2011 | Giordano et al. |
| 8,080,008 B2 | 12/2011 | Wham et al. |
| 8,086,315 B2 | 12/2011 | Schwartz et al. |
| 8,095,212 B2 | 1/2012 | Sato |
| 8,105,323 B2 | 1/2012 | Buysse et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,147,485 B2 | 4/2012 | Wham et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,801 B2 | 4/2012 | Goldberg et al. |
| 8,152,802 B2 | 4/2012 | Podhajsky et al. |
| 8,162,932 B2 | 4/2012 | Podhajsky et al. |
| 8,175,711 B2 | 5/2012 | Demarais et al. |
| 8,241,275 B2 | 8/2012 | Hong et al. |
| 8,273,084 B2 | 9/2012 | Kunis et al. |
| 8,340,763 B2 | 12/2012 | Levin et al. |
| 8,347,891 B2 | 1/2013 | Demarais et al. |
| 8,617,104 B2 | 12/2013 | Yribarren et al. |
| 8,702,619 B2 | 4/2014 | Wang |
| 8,768,470 B2 | 7/2014 | Deem et al. |
| 8,777,942 B2 | 7/2014 | Wu et al. |
| 8,876,813 B2 | 11/2014 | Min et al. |
| 8,888,773 B2 | 11/2014 | Chang et al. |
| 8,909,316 B2 | 12/2014 | Ng |
| 8,977,359 B2 | 3/2015 | Rossing |
| 8,998,894 B2 | 4/2015 | Mauch et al. |
| 9,002,446 B2 | 4/2015 | Wenzel et al. |
| 9,014,809 B2 | 4/2015 | Wenzel et al. |
| 9,014,821 B2 | 4/2015 | Wang |
| 9,022,948 B2 | 5/2015 | Wang |
| 9,028,472 B2 | 5/2015 | Mathur et al. |
| 9,037,259 B2 | 5/2015 | Mathur |
| 9,043,191 B2 | 5/2015 | Grady et al. |
| 9,060,755 B2 | 6/2015 | Buckley et al. |
| 9,084,610 B2 | 7/2015 | Goshgarian et al. |
| 9,119,600 B2 | 9/2015 | Richardson et al. |
| 9,168,094 B2 | 10/2015 | Lee et al. |
| 9,179,973 B2 | 11/2015 | Nabutovsky et al. |
| 9,186,212 B2 | 11/2015 | Nabutovsky et al. |
| 9,295,842 B2 | 3/2016 | Ghaffari et al. |
| 9,314,300 B2 | 4/2016 | Nabutovsky et al. |
| 9,375,154 B2 | 6/2016 | Wang |
| 9,427,283 B2 | 8/2016 | Nabutovsky et al. |
| 9,427,579 B2 | 8/2016 | Fain et al. |
| 9,554,850 B2 | 1/2017 | Lee et al. |
| 9,561,070 B2 | 2/2017 | Brotz et al. |
| 9,579,030 B2 | 2/2017 | Scheuermann et al. |
| 9,622,808 B2 | 4/2017 | Beller et al. |
| 10,786,306 B2 | 9/2020 | Coates et al. |
| 2001/0014802 A1 | 8/2001 | Tu |
| 2002/0091385 A1 | 7/2002 | Paton et al. |
| 2002/0161422 A1 | 10/2002 | Swanson et al. |
| 2002/0165532 A1 | 11/2002 | Hill et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0065322 A1 | 4/2003 | Panescu et al. |
| 2003/0074039 A1 | 4/2003 | Puskas |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0068304 A1 | 4/2004 | Paton et al. |
| 2004/0122420 A1 | 6/2004 | Amoah |
| 2004/0172111 A1 | 9/2004 | Hijii et al. |
| 2004/0215186 A1 | 10/2004 | Cornelius et al. |
| 2005/0021020 A1 | 1/2005 | Blaha |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0228460 A1 | 10/2005 | Levin et al. |
| 2005/0283148 A1 | 12/2005 | Janssen et al. |
| 2005/0288730 A1 | 12/2005 | Deem et al. |
| 2006/0004301 A1 | 1/2006 | Kasevich |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0106375 A1 | 5/2006 | Werneth et al. |
| 2006/0142753 A1 | 6/2006 | Francischelli et al. |
| 2006/0161148 A1 | 7/2006 | Behnke |
| 2006/0206150 A1 | 9/2006 | Demarais et al. |
| 2006/0271111 A1 | 11/2006 | Demarais et al. |
| 2007/0016274 A1 | 1/2007 | Boveja et al. |
| 2007/0083193 A1 | 4/2007 | Werneth et al. |

(56) References Cited

U.S. PATENT DOCUMENTS

| | | |
|---|---|---|
| 2007/0083195 A1 | 4/2007 | Werneth et al. |
| 2007/0100390 A1 | 5/2007 | Danaek et al. |
| 2007/0112342 A1 | 5/2007 | Pearson et al. |
| 2007/0129720 A1 | 6/2007 | Demarais et al. |
| 2007/0167943 A1 | 7/2007 | Janssen et al. |
| 2007/0203481 A1 | 8/2007 | Gregg et al. |
| 2007/0208333 A1 | 9/2007 | Uchida et al. |
| 2007/0260112 A1* | 11/2007 | Rahmani ......... A61B 17/12013 600/104 |
| 2007/0265687 A1 | 11/2007 | Deem et al. |
| 2007/0270795 A1 | 11/2007 | Francischelli et al. |
| 2008/0015562 A1 | 1/2008 | Hong et al. |
| 2008/0071257 A1 | 3/2008 | Kotmel et al. |
| 2008/0077126 A1 | 3/2008 | Rashidi |
| 2008/0101356 A1 | 5/2008 | Babbar et al. |
| 2008/0147057 A1 | 6/2008 | Eisele |
| 2008/0188912 A1 | 8/2008 | Stone et al. |
| 2008/0188913 A1 | 8/2008 | Stone et al. |
| 2008/0228181 A1 | 9/2008 | Godara et al. |
| 2008/0255539 A1 | 10/2008 | Booth |
| 2008/0262489 A1 | 10/2008 | Steinke |
| 2008/0281312 A1 | 11/2008 | Werneth et al. |
| 2008/0281322 A1 | 11/2008 | Sherman et al. |
| 2008/0300589 A1 | 12/2008 | Paul et al. |
| 2008/0319513 A1 | 12/2008 | Pu et al. |
| 2009/0030477 A1 | 1/2009 | Jarrard |
| 2009/0036948 A1 | 2/2009 | Levin et al. |
| 2009/0178289 A1* | 7/2009 | Sakai ................ A61B 5/1076 33/543.1 |
| 2009/0182323 A1 | 7/2009 | Eder et al. |
| 2009/0182325 A1 | 7/2009 | Werneth et al. |
| 2009/0204134 A1* | 8/2009 | Kassab ............... A61B 5/053 600/587 |
| 2009/0299365 A1 | 12/2009 | Stewart et al. |
| 2010/0137860 A1 | 6/2010 | Demarais et al. |
| 2010/0137952 A1 | 6/2010 | Demarais et al. |
| 2010/0179533 A1 | 7/2010 | Podhaisky |
| 2010/0179538 A1 | 7/2010 | Podhaisky |
| 2010/0191112 A1 | 7/2010 | Demarais et al. |
| 2010/0211063 A1 | 8/2010 | Wham et al. |
| 2010/0222786 A1* | 9/2010 | Kassab ............... A61B 5/0538 606/127 |
| 2010/0222851 A1 | 9/2010 | Deem et al. |
| 2010/0222854 A1 | 9/2010 | Demarais et al. |
| 2010/0228247 A1 | 9/2010 | Paul et al. |
| 2010/0324548 A1 | 12/2010 | Godara et al. |
| 2011/0077641 A1 | 3/2011 | Dunning |
| 2011/0087214 A1 | 4/2011 | Giordano et al. |
| 2011/0087217 A1 | 4/2011 | Yates et al. |
| 2011/0112400 A1 | 5/2011 | Emery et al. |
| 2011/0130755 A1 | 6/2011 | Bhushan et al. |
| 2011/0184378 A1 | 7/2011 | Kobayashi et al. |
| 2011/0190755 A1 | 8/2011 | Mathur et al. |
| 2011/0230876 A1 | 9/2011 | Hong et al. |
| 2011/0264086 A1 | 10/2011 | Ingle |
| 2011/0270120 A1 | 11/2011 | McFarlin et al. |
| 2011/0270237 A1 | 11/2011 | Werneth et al. |
| 2011/0270247 A1 | 11/2011 | Sherman |
| 2011/0306851 A1 | 12/2011 | Wang |
| 2012/0004656 A1 | 1/2012 | Jackson et al. |
| 2012/0029504 A1 | 2/2012 | Afonso et al. |
| 2012/0041502 A1 | 2/2012 | Schwartz et al. |
| 2012/0089047 A1* | 4/2012 | Ryba ................... A61B 18/02 600/300 |
| 2012/0095461 A1 | 4/2012 | Herscher et al. |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0123400 A1 | 5/2012 | Francischelli et al. |
| 2012/0130289 A1 | 5/2012 | Demarais et al. |
| 2012/0130345 A1 | 5/2012 | Levin et al. |
| 2012/0136346 A1 | 5/2012 | Condie et al. |
| 2012/0136348 A1 | 5/2012 | Condie et al. |
| 2012/0136350 A1 | 5/2012 | Goshgarian et al. |
| 2012/0143097 A1 | 6/2012 | Pike, Jr. |
| 2012/0143293 A1 | 6/2012 | Mauch et al. |
| 2012/0150169 A1 | 6/2012 | Zielinksi et al. |
| 2012/0172837 A1 | 6/2012 | Demarais et al. |
| 2012/0172870 A1 | 7/2012 | Jenson et al. |
| 2012/0191079 A1 | 7/2012 | Moll et al. |
| 2012/0197243 A1 | 8/2012 | Sherman et al. |
| 2012/0197246 A1 | 8/2012 | Mauch |
| 2012/0296232 A1 | 11/2012 | Ng |
| 2012/0296329 A1 | 11/2012 | Ng |
| 2012/0310241 A1 | 12/2012 | Orszulak |
| 2013/0006228 A1 | 1/2013 | Johnson et al. |
| 2013/0006235 A1 | 1/2013 | Podhajsky et al. |
| 2013/0035740 A1* | 2/2013 | Sharma ............... A61N 1/0517 607/40 |
| 2013/0085489 A1 | 4/2013 | Fain et al. |
| 2013/0165764 A1 | 6/2013 | Scheuermann et al. |
| 2013/0172878 A1 | 7/2013 | Smith |
| 2013/0218029 A1 | 8/2013 | Cholette et al. |
| 2013/0231659 A1 | 9/2013 | Hill et al. |
| 2013/0274614 A1 | 10/2013 | Shimada et al. |
| 2013/0282001 A1 | 10/2013 | Hezi-Yamit et al. |
| 2013/0296840 A1 | 11/2013 | Condie et al. |
| 2013/0310820 A1 | 11/2013 | Fernandez et al. |
| 2014/0012133 A1 | 1/2014 | Sverdlik et al. |
| 2014/0025069 A1 | 1/2014 | Willard et al. |
| 2014/0066803 A1 | 3/2014 | Choi |
| 2014/0073903 A1 | 3/2014 | Weber et al. |
| 2014/0074089 A1 | 3/2014 | Nishii |
| 2014/0128865 A1 | 5/2014 | Gross |
| 2014/0194866 A1 | 7/2014 | Wang |
| 2014/0213873 A1 | 7/2014 | Wang |
| 2014/0221805 A1 | 8/2014 | Wang |
| 2014/0228614 A1 | 8/2014 | Stopek |
| 2014/0228829 A1 | 8/2014 | Schmitt et al. |
| 2014/0228858 A1 | 8/2014 | Stopek |
| 2014/0236137 A1 | 8/2014 | Tran et al. |
| 2014/0236138 A1 | 8/2014 | Tran et al. |
| 2014/0246465 A1 | 9/2014 | Peterson et al. |
| 2014/0249524 A1 | 9/2014 | Kocur |
| 2014/0257266 A1 | 9/2014 | Kasprzyk et al. |
| 2014/0266235 A1 | 9/2014 | Mathur |
| 2014/0275924 A1 | 9/2014 | Min et al. |
| 2014/0276124 A1 | 9/2014 | Cholette et al. |
| 2014/0276718 A1 | 9/2014 | Turovskiy et al. |
| 2014/0276733 A1 | 9/2014 | VanScoy et al. |
| 2014/0276742 A1 | 9/2014 | Nabutovsky et al. |
| 2014/0276746 A1 | 9/2014 | Nabutovsky et al. |
| 2014/0276755 A1 | 9/2014 | Cao et al. |
| 2014/0276762 A1 | 9/2014 | Parsonage |
| 2014/0276766 A1 | 9/2014 | Bratz et al. |
| 2014/0276767 A1 | 9/2014 | Bratz et al. |
| 2014/0276773 A1 | 9/2014 | Bratz et al. |
| 2014/0316400 A1 | 10/2014 | Blix et al. |
| 2014/0316496 A1 | 10/2014 | Masson et al. |
| 2014/0330266 A1 | 11/2014 | Thompson et al. |
| 2014/0330267 A1 | 11/2014 | Harrington |
| 2014/0336637 A1 | 11/2014 | Agrawal et al. |
| 2015/0005764 A1 | 1/2015 | Hanson et al. |
| 2015/0005769 A1* | 1/2015 | Klink ................ A61B 18/1477 606/46 |
| 2015/0018656 A1 | 1/2015 | Min et al. |
| 2015/0025524 A1 | 1/2015 | Nabutovsky |
| 2015/0112329 A1 | 4/2015 | Ng |
| 2015/0119674 A1 | 4/2015 | Fischell et al. |
| 2015/0173673 A1 | 6/2015 | Toth et al. |
| 2015/0201997 A1 | 7/2015 | Osypka |
| 2015/0216590 A1 | 8/2015 | Wang et al. |
| 2015/0223877 A1 | 8/2015 | Behar et al. |
| 2015/0224326 A1 | 8/2015 | Toth et al. |
| 2015/0245867 A1 | 9/2015 | Gross |
| 2015/0289929 A1 | 10/2015 | Toth et al. |
| 2015/0305808 A1* | 10/2015 | Ku ..................... A61B 18/1492 606/41 |
| 2015/0366609 A1 | 12/2015 | Richardson et al. |
| 2016/0000345 A1 | 1/2016 | Kobayashi et al. |
| 2016/0029960 A1 | 2/2016 | Toth et al. |
| 2016/0038028 A1 | 2/2016 | Buelna et al. |
| 2016/0081744 A1 | 3/2016 | Wang |

(56) References Cited

U.S. PATENT DOCUMENTS

| | | | |
|---|---|---|---|
| 2016/0095535 A1* | 4/2016 | Hettrick | A61B 18/1206 600/381 |
| 2016/0106498 A1 | 4/2016 | Highsmith et al. | |
| 2016/0184010 A1 | 6/2016 | Nabutovsky et al. | |
| 2016/0213262 A1 | 7/2016 | Ghaffari et al. | |
| 2016/0213424 A1 | 7/2016 | Ghaffari et al. | |
| 2016/0310201 A1 | 10/2016 | Brotz et al. | |
| 2016/0324572 A1 | 11/2016 | Gross et al. | |
| 2016/0331451 A1 | 11/2016 | Nabutovsky et al. | |
| 2016/0331453 A1 | 11/2016 | Fain et al. | |
| 2016/0374568 A1 | 12/2016 | Wang | |
| 2017/0007157 A1 | 1/2017 | Gross et al. | |
| 2017/0007158 A1 | 1/2017 | Gross et al. | |
| 2017/0095291 A1 | 4/2017 | Harrington et al. | |
| 2017/0215794 A1 | 8/2017 | Trudel et al. | |
| 2017/0215950 A1 | 8/2017 | Gross et al. | |
| 2019/0069949 A1* | 3/2019 | Vrba | A61B 18/02 |
| 2019/0151013 A1 | 5/2019 | Hettrick et al. | |
| 2019/0175035 A1* | 6/2019 | Van Der Horst | A61B 8/4477 |
| 2019/0223754 A1 | 7/2019 | Gunasekaran et al. | |
| 2019/0223945 A1 | 7/2019 | Coates et al. | |
| 2019/0223946 A1 | 7/2019 | Coates et al. | |
| 2020/0129087 A1* | 4/2020 | Sweeney | A61B 5/1076 |

FOREIGN PATENT DOCUMENTS

| | | |
|---|---|---|
| EP | 1366724 A1 | 12/2003 |
| EP | 2316371 A1 | 5/2011 |
| EP | 2460486 A1 | 6/2012 |
| EP | 2594193 A2 | 5/2013 |
| EP | 2613704 A2 | 7/2013 |
| EP | 2747691 A1 | 7/2014 |
| EP | 2797535 A1 | 11/2014 |
| EP | 2457615 | 12/2014 |
| EP | 2852339 A1 | 4/2015 |
| EP | 2866645 A1 | 5/2015 |
| EP | 2887900 A1 | 7/2015 |
| EP | 2907464 A1 | 8/2015 |
| EP | 2914192 A2 | 9/2015 |
| EP | 2914334 A2 | 9/2015 |
| EP | 2967383 A1 | 1/2016 |
| EP | 2967702 A1 | 1/2016 |
| EP | 2967703 A1 | 1/2016 |
| EP | 2967728 A1 | 1/2016 |
| EP | 2967729 A1 | 1/2016 |
| EP | 2967733 A2 | 1/2016 |
| EP | 2968931 A1 | 1/2016 |
| EP | 2978372 A2 | 2/2016 |
| EP | 2991575 A1 | 3/2016 |
| EP | 3011899 A1 | 4/2016 |
| EP | 3028628 A1 | 6/2016 |
| EP | 3089686 A2 | 11/2016 |
| EP | 3158961 A1 | 4/2017 |
| EP | 2934357 | 11/2017 |
| JP | H08504531 A | 5/1996 |
| JP | H1071037 A | 3/1998 |
| JP | 2001518808 A | 10/2001 |
| JP | 2005278739 A | 10/2005 |
| JP | 2008515544 A | 5/2008 |
| JP | 2009539565 A | 11/2009 |
| JP | 2010162163 A | 7/2010 |
| JP | 2010533513 A | 10/2010 |
| JP | 2011505929 A | 3/2011 |
| JP | 6122206 B2 | 4/2017 |
| JP | 2017536187 A | 12/2017 |
| WO | 1993008757 A1 | 5/1993 |
| WO | 1994007446 A1 | 4/1994 |
| WO | 1994010922 A1 | 5/1994 |
| WO | 1995025472 A1 | 9/1995 |
| WO | 1995031142 A1 | 11/1995 |
| WO | 1996000036 A1 | 1/1996 |
| WO | 1996039086 A1 | 12/1996 |
| WO | 1997004702 A1 | 2/1997 |
| WO | 1997036548 A1 | 10/1997 |
| WO | 1997040882 A2 | 11/1997 |
| WO | 1998042403 A1 | 10/1998 |
| WO | 1999000060 A1 | 1/1999 |
| WO | 1999060923 A1 | 12/1999 |
| WO | 2000001313 A1 | 1/2000 |
| WO | 2000015130 A2 | 3/2000 |
| WO | 2001019270 A1 | 3/2001 |
| WO | 2001022897 A1 | 4/2001 |
| WO | 2001070114 A1 | 9/2001 |
| WO | 2002087679 A2 | 11/2002 |
| WO | 2003022167 A1 | 3/2003 |
| WO | 2003082080 A2 | 10/2003 |
| WO | 2005030072 A1 | 4/2005 |
| WO | 2005041748 A2 | 5/2005 |
| WO | 2005051215 A1 | 6/2005 |
| WO | 2005110528 A1 | 11/2005 |
| WO | 2006041881 A2 | 4/2006 |
| WO | 2006080982 A1 | 8/2006 |
| WO | 2006105121 A2 | 10/2006 |
| WO | 2007001981 A2 | 1/2007 |
| WO | 2007008954 A2 | 1/2007 |
| WO | 2007067941 A2 | 6/2007 |
| WO | 2007078997 A2 | 7/2007 |
| WO | 2007135431 A2 | 11/2007 |
| WO | 2008003058 A2 | 1/2008 |
| WO | 2008049084 A2 | 4/2008 |
| WO | 2008101356 A1 | 8/2008 |
| WO | 2010078175 A1 | 7/2010 |
| WO | 2011017168 A2 | 2/2011 |
| WO | 2011089935 A2 | 7/2011 |
| WO | 2011126580 A2 | 10/2011 |
| WO | 2011144911 A1 | 11/2011 |
| WO | 2012024631 A1 | 2/2012 |
| WO | 2012033974 A2 | 3/2012 |
| WO | 2012054762 A2 | 4/2012 |
| WO | 2012061159 A1 | 5/2012 |
| WO | 2012068471 A1 | 5/2012 |
| WO | WO2012061153 | 5/2012 |
| WO | WO2012061161 | 5/2012 |
| WO | 2012158864 A1 | 11/2012 |
| WO | 2013030738 A1 | 3/2013 |
| WO | 2013030743 A1 | 3/2013 |
| WO | 2013074813 A1 | 5/2013 |
| WO | 2013101485 A1 | 7/2013 |
| WO | 2013112844 A2 | 8/2013 |
| WO | 2014012282 A1 | 1/2014 |
| WO | 2014029355 A1 | 2/2014 |
| WO | 2014059165 A2 | 4/2014 |
| WO | 2014124241 A1 | 8/2014 |
| WO | 2014149550 A2 | 9/2014 |
| WO | 2014149552 A1 | 9/2014 |
| WO | 2014149553 A1 | 9/2014 |
| WO | 2014149690 A2 | 9/2014 |
| WO | 2014150441 A2 | 9/2014 |
| WO | 2014150455 A1 | 9/2014 |
| WO | 2014158708 A1 | 10/2014 |
| WO | 2014158713 A1 | 10/2014 |
| WO | 2014163990 A1 | 10/2014 |
| WO | 2014179110 A1 | 11/2014 |
| WO | 2014179768 A1 | 11/2014 |
| WO | 2014182946 A2 | 11/2014 |
| WO | WO2015113027 | 7/2015 |
| WO | WO2015143372 | 9/2015 |
| WO | 2016090175 | 6/2016 |
| WO | WO2017012907 | 1/2017 |

OTHER PUBLICATIONS

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Clinc, 2000, vol. 12, No. 4, pp. 323-327.

(56) References Cited

OTHER PUBLICATIONS

Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Brown, "Electrical impedance tomography (EIT): a review," Journal of Medical Engineering and Technology, vol. 27, No. 3, May/Jun. 2003, pp. 107-108.
Esler et al., "Renal Denervation: Not as Easy as it Looks," Science Translational Medicine, vol. 7, No. 285, Apr. 29, 2015, 4 pages.

Mahfoud et al., "Efficacy and Safety of Catheter-Based Radiofrequency Renal Denervation in Stented Renal Arteries," Circ Cardiovasc Interv. 2014; 7 :813-818.
Wolf et al., "Noninvasive assessment of lung volume: Respiratory inductance plethysmography and electrical impedance tomography." Crit Care Med 2005; vol. 33(3) Supplement.S163-S169.
Coulombe et al., "A Parametric Model of the Relationship Between EIT and Total Lung Volume." Physiol Meas 2005;26(4):401-411.
Zhang et al., "EIT Images of Ventilation: What Contributes to the Resistivity Changes?" Physiol. Meas., 2005, 26(2): S81-S92.
Brown, "Electrical impedance tomography (EIT): a review," Journal of Medical Engineering & Technology. 2003; 27:97-108.
U.S. Appl. No. 62/588,215, by Hettrick et al, filed Nov. 17, 2017.
U.S. Appl. No. 15/965,687, by Coates et al., filed Apr. 27, 2018.
U.S. Appl. No. 15/965,692, by Coates et al., filed Apr. 27, 2018.
U.S. Appl. No. 15/965,675, by Coates et al., filed Apr. 27, 2018.
Ewen et al., "Anatomical and procedural determinants of catheter-based renal denervation." Cardiovascular Revascularization Medicine, May 25, 2016, vol. 17, pp. 474-479.
International Search Report and Written Opinion from counterpart PCT Application No. PCT/US2019/014059, mailed May 7, 2019, 11 pages.
International Preliminary Report on Patentability from counterpart PCT Application No. PCT/US2019/014059, mailed Jul. 28, 2020, 8 pages.
"2011 Edison Award Winners," Edison Awards: Honoring Innovations & Innovators, 2011, 6 pp., Retrieved from the Internet: URL: http://www.edisonawards.com/BestNewProduct_2011.php on Oct. 7, 2013.
"2012 Top 10 Advances in Heart Disease And Stroke Research: American Heart Association/America Stroke Association Top 10 Research Report," American Heart Association, Dec. 17, 2012, 5 pp., Retrieved from the Internet: URL: http://newsroom.heart.org/news/2012-top-10-advances-in-heart-241901.
"Ardian(R) Receives 2010 EuroPCR Innovation Award and Demonstrates Further Durability of Renal Denervation Treatment for Hypertension," PR Newswire, Jun. 3, 2010, 2 pp, Retrieved from the Internet: URL: http://www.prnewswire.com/news-releases/ardianr-receives-2010-europcr-innovation-awardand-demonstrates-further-durability-of-renal-denervation-treatment-for-hypertension-95545014.html.
"Boston Scientific to Acquire Vessix Vascular, Inc.: Company to Strengthen Hypertension Program with Acquisition of Renal Denervation Technology," Boston Scientific: Advancing Science for Life-Investor Relations, Nov. 8, 2012, 2 pp, Retrieved from the Internet: URL: http://phx.corporateir.net/phoenix.zhtml?c=62272&p=irol-newsArticle&id=1756108.
"Cleveland Clinic Unveils Top 10 Medical Innovations for 2012: Experts Predict Ten Emerging Technologies that will Shape Health Care Next Year," Cleveland Clinic, Oct. 6, 2011, 2 pp., Retrieved from the Internet: URL: http://my.clevelandclinic.org/media_relations/library/2011/2011-10-6-cleveland-clinicunveils-top-10-medical-innovations-for-2012.aspx.
"Does Renal Denervation Represent a New Treatment Option for Resistant Hypertension?" Interventional News, Aug. 3, 2010, 2 pp., Retrieved from the Internet: URL: http://www.cxvascular.com/in-latestnews/interventional-news-latest-news/does-renal-denervation-represent-a-new-treatmentoption-for-resistant-hypertension.
"Impact of Renal Sympathetic Denervation of Chronic Hypertension (SAVE)" Mount Sinai School of Medicine Clinical Trial, Mar. 2013, 11 pp., Retrieved from the Internet: URL: http://clinicaltrials.gov/ct2/show/NCT01628198.
"Neurotech Reports Announces Winners of Gold Electrode Awards," Neurotech Business Report, 2009, 1 pp. Retrieved from the Internet: URL: http://www.neurotechreports.com/pages/goldelectrodes09.html on Oct. 7, 2013.
"Quick. Consistent. Controlled." OneShot renal Denervation System, Brochure, Covidien: Positive Results for Life, 2013, 4 pp. (Applicant points out, in accordance with MPEP 609.04(a), that the year of publication, 2013, is sufficiently earlier than the effective U.S. filing date, so that the particular month of publication is not in issue).

(56) References Cited

OTHER PUBLICATIONS

"Renal Denervation Technology of Vessix Vascular, Inc. been acquired by Boston Scientific Corporation (BSX) to pay up to $425 Million," Vessix Vascular Pharmaceutical Intelligence: A blog specializing in Pharmaceutical Intelligence and Analytics, Nov. 8, 2012, 21 pp., Retrieved from the Internet: URL: http://pharmaceuticalintell igence.com/tag/vessix-vascular/.
"Symplicity RON System Common Q&A," Renal Denervation (RON): Novel Catheter-Based Treatment for Hypertension, 2011, 4 pp, Retrieved from the Internet: URL: http://www.medtronic.com/rdn/mediakit/RDN%20FAQ.pdf. (Applicant points out, in accordance with MPEP 609.04(a), that the year of publication, 2011, is sufficiently earlier than the effective U.S. filing date, so that the particular month of publication is not in issue).
"The Edison Awards TM," Edison Awards: Honoring Innovations & Innovators, 2013, 2 pp, Retrieved from the Internet: URL: http://www.edisonawards.com/Awards.php. (Applicant points out, in accordance with MPEP 609.04(a), that the year of publication, 2013, is sufficiently earlier than the effective U.S. filing date, so that the particular month of publication is not in issue).
"The Future of Renal Denervation for the Treatment of Resistant Hypertension," St. Jude Medical, Inc., 2012, 12 pp. (Applicant points out, in accordance with MPEP 609.04(a), that the year of publication, 2012, is sufficiently earlier than the effective U.S. filing date, so that the particular month of publication is not in issue).
"ThermoCool: Irrigated Catheter and Integrated Ablation System," Biosense Webster Inc., 2006, 6 pp. (Applicant points out, in accordance with MPEP 609.04(a), that the year of publication, 2006, is sufficiently earlier than the effective U.S. filing date, so that the particular month of publication is not in issue).
"Turning Innovation Into Quality Care," Iberis-Renal Sympathetic Denervation System, Brochure, Terumo Europe N.V., 2013, Europe, 3 pp. (Applicant points out, in accordance with MPEP 609.04(a), that the year of publication, 2013, is sufficiently earlier than the effective U.S. filing date, so that the particular month of publication is not in issue).
"Ureter," https://en.wikipedia.org/wiki/Ureter, Retrieved from the Internet Jan. 16, 2022, 10 pgs.
"Vessix Renal Denervation System: So Advanced It's Simple," Brochure, Boston Scientific: Advancing Science for Life, 2013, 6 pp. (Applicant points out, in accordance with MPEP 609.04(a), that the year of publication, 2013, is sufficiently earlier than the effective U.S. filing date, so that the particular month of publication is not in issue).
Ahmed et al., "Renal Sympathetic Denervation Using an Irrigated Radiofrequency Ablation Catheter for the Management of Drug-Resistant Hypertension," JACC Cardiovascular Interventions, vol. 5, No. 7, Jul. 2012, pp. 758-765.
Asbell et al., "Conductive Keratoplasty For The Correction of Hyperopia," Transactions of the American Ophthalmological Society, Nov. 9, 2001, vol. 99, pp. 79-87.
Avitall et al., "The Creation of Linear Contiguous Lesions in the Atria with an Expandable Loop Catheter," Journal of the American College of Cardiology, Mar. 15, 1999, vol. 33, No. 4, pp. 972-984.
Badoer, "Cardiac Afferents Play the Dominant Role in Renal Nerve Inhibition Elicited by Volume Expansion in the Rabbit," American Journal of Physiology, The American Physiological Society, vol. 274, Issue 2, Feb. 1998, pp. R383-R388.
Beale et al., "Minimally Invasive Treatment for Varicose Veins: A Review of Endovenous Laser Treatment and Radiofrequency Ablation". Lower Extremity Wounds, vol. 3, No. 4, 2004, pp. 188-197. (Applicant points out, in accordance with MPEP 609.04(a), that the year of publication, 2004, is sufficiently earlier than the effective U.S. filing date, so that the particular month of publication is not in issue).
Bengel, "Serial Assessment of Sympathetic Reinnervation After Orthotopic Heart Transplantation: A Longitudinal Study Using PET and C-11 Hydroxyephedrine," Circulation, vol. 99, Apr. 13, 1999, pp. 1866-1871.
Benito et al. "Radiofrequency Catheter Ablation of Accessory Pathways in Infants," Heart, vol. 78, 1997, pp. 160-162. (Applicant points out, in accordance with MPEP 609.04(a), that the year of publication, 1997, is sufficiently earlier than the effective U.S. filing date, so that the particular month of publication is not in issue).
Bettmann, "Carotid Stenting and Angioplasty: A Statement for Healthcare Professionals From the Councils on Cardiovascular Radiology, Stroke, Cardia-Thoracic and Vascular Surgery, Epidemiology and Prevention, and Clinical Cardiology, American Heart Association," Stroke, vol. 97, Issue 1, Jan. 1998, pp. 336-338.
Blessing et al., "Cardiac Ablation and Renal Denervation Systems Have Distinct Purposes and Different Technical Requirements," JACC Cardiovascular Interventions, vol. 6, No. 3, 2013, 1 pp. (Applicant points out, in accordance with MPEP 609.04(a), that the year of publication, 2013, is sufficiently earlier than the effective U.S. filing date, so that the particular month of publication is not in issue).
Bohm et al., "First report of the Global SYMPLICITY Registry on the Effect of Renal Artery Denervation in Patients with Uncontrolled Hypertension," Hypertension, Apr. 2015, vol. 65, No. 4, pp. 766-774.
Bohm et al., "Rationale and Design of a Large Registry on Renal Denervation: The Global SYMPLICITY Registry," EuroIntervention, vol. 9, Issue 4, Aug. 2013, pp. 484-492.
Brosky, "EuroPCR 2013: CE-Approved Devices Line Up for Renal Denervation Approval," Medical Device Daily, May 28, 2013, 3 pp., Retrieved from the Internet: URL: http://www.medicaldevicedaily.com/servlet/com.accumedia.web.Dispatcher?next=bioWorldHeadlines_article&forceid=83002.
Chinushi et al., "Blood Pressure and Autonomic Responses to Electrical Stimulation of the Renal Arterial Nerves Before and After Ablation of the Renal Artery." Hypertension, vol. 61, Issue 2, Feb. 2013, pp. 450-456.
ClinicalTrials.gov, "Renal Denervation in Patients with uncontrolled Hypertension in Chinese," The Second People's Hospital of Chengdu, Apr. 2011, Retrieved from the Internet: URL: www.clinicaltrials.gov/ct2/show/NCT01390831, 5 pp.
Davis et al., "Effectiveness of Renal Denervation Therapy for Resistant Hypertension." Journal of the American College of Cardiology, vol. 62, No. 3, Jul. 16, 2013, pp. 231-241.
Dibona, G.F. "Sympathetic Nervous System and Kidney in Hypertension." Nephrol and Hypertension, vol. 11, 2002, pp. 197-200. (Applicant points out, in accordance with MPEP 609.04(a), that the year of publication, 2002, is sufficiently earlier than the effective U.S. filing date, so that the particular month of publication is not in issue).
Dodge Jr., et al., "Lumen Diameter of Normal Human Coronary Arteries—Influence of Age, Sex, Anatomic Variation, and Left Ventricular Hypertrophy or Dilation," Circulation, Jul. 1992, vol. 86 No. 1, pp. 232-246.
Doumas, Michael et al., "Renal Nerve Ablation for Resistant Hypertension: The Dust Has Not Yet Settled." The Journal of Clinical Hypertension, Jun. 2014, vol. 16, No. 6, pp. 399-400.
Dubuc et al., "Feasibility of Cardiac Cryoablation Using a Transvenous Steerable Electrode Catheter," Journal of Interventional Cardiac Electrophysiology, vol. 2, Feb. 5, 1998, pp. 285-292.
Excerpt of Operator's Manual of Boston Scientific's EPT-1000 XP Cardiac Ablation Controller & Accessories, Version of Apr. 2003, 6 pp.
Excerpt of Operator's Manual of Boston Scientific's Maestro 30000 Cardiac Ablation System, Version of Oct. 17, 2005, 4 pp.
Geisler et al., "Cost-Effectiveness and Clinical Effectiveness of Catheter-Based Renal Denervation for Resistant Hypertension," Journal of the American College of Cardiology, vol. 60, No. 14, Oct. 2, 2012, pp. 1271-1277.
Gertner, "Meet The Tech Duo That's Revitalizing The Medical Device Industry." Fast Company, Apr. 15, 2013, 11 pages, Retrieved from the Internet: URL:http://www.fastcompany.com/3007845/meettech-duo-thats-revitalizing-medical-device-industry.
Golwyn, D. H., Jr., et al. "Percutaneous Transcatheter Renal Ablation with Absolute Ethanol for Uncontrolled Hypertension or Nephrotic

(56) References Cited

OTHER PUBLICATIONS

Syndrome: Results in 11 Patients with End-Stage Renal Disease," Journal of Vascular and Interventional Radiology, vol. 8, Issue 4, Jul. 1997, pp. 527-533.

Hall et al., "Combined Embolization And Percutaneous Radiofrequency Ablation Of A Solid Renal Tumor," American Journal of Roentgenology, vol. 17, No. 6, Jun. 2000, pp. 1592-1594.

Han et al., "Renal Artery Ebolization with Diluted Hot Contrast Medium: An Experimental Study." Journal of Vascular and Interventional Radiology, vol. 12, Issue 7, Jul. 1, 2001, pp. 862-868.

Hansen et al. "The Transplanted Human Kidney Does Not Achieve Functional Reinnervation," Clinical Science, vol. 87, Issue 1, Jul. 1994, pp. 13-19.

Hendee et al. "Use of Animals in Biomedical Research: The Challenge and Response." American Medical Association White Paper, Jun. 21, 1988, 39 pp.

Hering et al., "Chronic Kidney Disease: Role of Sympathetic Nervous System Activation and Potential Benefits of Renal Denervation," EuroIntervention, vol. 9, Supplement R, 2013, pp. R127-R135. (Applicant points out, in accordance with MPEP 609.04(a), that the year of publication, 2013, is sufficiently earlier than the effective U.S. filing date, so that the particular month of publication is not in issue).

Holmes et al., "Pulmonary Vein Stenosis Complicating Ablation for Atrial Fibrillation: Clinical Spectrum and Interventional Considerations," JACC: Cardiovascular Interventions, vol. 2, No. 4, Apr. 2009, pp. 267-276.

Huang et al., "Renal Denervation Prevents and Reverses Hyperinsulinemia-Induced Hypertension in Rats," Hypertension, vol. 32, Issue 2, Aug. 1998, pp. 249-254.

Imimdtanz, "Medtronic Awarded Industry's Highest Honor For Renal Denervation System" The Official Blog of Medtronic Australasia, Nov. 12, 2012, 2 pp., Retrieved from the Internet: URL: http://97waterlooroad.wordpress.com/2012/11/12/medtronic-awarded-industrys-highesthonour-for-renal-denervation-system/.

Jv et al., "Wall Shear Stress Oscillation and its Gradient in the Normal Left Coronary Artery Tree Bifurcations, " Hippokratia, Jan.-Mar. 2014, vol. 18, No. 1, pp. 12-16.

Kaiser, "AHA Lists Year's Big Advances in CV Research," MEDPAGE Today, Dec. 18, 2012, 5 pp., Retrieved from the Internet: URL: http://www.medpagetoday.com/Cardiology/PCI/36509.

Kandarpa et al., "Handbook of Interventional Radiologic Procedures," Third Edition, 2002, pp. 194-210. (Applicant points out, in accordance with MPEP 609.04(a), that the year of publication, 2002, is sufficiently earlier than the effective U.S. filing date, so that the particular month of publication is not in issue).

Knight et al., "Choosing the Optimal Wall Shear Parameter for the Prediction of Plaque Location—A Patient-Specific Computational Study in Human Right Coronary Arteries," Atherosclerosis, Aug. 1, 2010, vol. 211, Issue 2, pp. 445-450.

Kompanowska et al., "Early Effects of Renal Denervation in the Anaesthetised Rat: Natriuresis and Increased Cortical Blood Flow," Journal of Physiology, vol. 531, No. 2, 2001, pp. 527-534. (Applicant points out, in accordance with MPEP 609.04(a), that the year of publication, 2001, is sufficiently earlier than the effective U.S. filing date, so that the particular month of publication is not in issue).

Lee et al. "Ultrasonic Energy in Endoscopic Surgery." Yonsei Medical Journal, vol. 40, No. 6, Dec. 3, 1999, pp. 545-549.

Linz et al., "Renal Denervation Suppresses Ventricular Arrhythmias During Acute Ventricular Ischemia in Pigs" Heart Rhythm, vol. 10, Issue 10, Oct. 1, 2013, pp. 1525-1530.

Lustgarten et al., "Cryothermal Ablation: Mechanism of Tissue Injury and Current Experience in the Treatment of Tachyarrhythmias." Progress in Cardiovascular Diseases, vol. 41, Issue 6, May-Jun. 1999, pp. 481-498.

Mabin et al., "First Experience with Endovascular Ultrasound Renal Denervation for the Treatment of Resistant Hypertension." EuroIntervention, vol. 8, May 2012, pp. 57-61.

Mahfoud et al., "Ambulatory Blood Pressure Changes after Renal Sympathetic Denervation in Patients with Resistant Hypertension," Circulation, May 2013, pp. 132-140.

Mahfoud et al., "Expert Consensus Document from the European Society of Cardiology on Catheter-Based Renal Denervation," European Heart Journal, vol. 34, Jul. 2013, pp. 2149-2157.

Mahfoud et al., "Renal Hemodynamics and Renal Function After Catheter-Based Renal Sympathetic Denervation in Patients With Resistant Hypertension." Hypertension, Aug. 2012, pp. 419-424.

MedicalDictionary.com, "Definition of 'Animal Model'" http://medical-dictionary.com (search "Animal Model," Retrieved from the Internet Nov. 11, 2021, 1 pp.

Medtronic, Inc., Annual Report (Form 10-K), Jun. 28, 2011, 44 pp.

Messerli et al. "Renal Denervation for Resistant Hypertension: Dead or Alive?" Healio: Cardiology Today's Intervention, Oct. 29, 2013, 2 pages.

Millard et al, "Renal Embolization for Ablation of Function in Renal Failure and Hypertension," Postgraduate Medical Journal, vol. 65, May 1989, pp. 729-734.

Miller, "Finding A Future For Renal Denervation With Better Controlled Trials." Pharma & Medtech Business Intelligence, Article# 01141006003, Oct. 6, 2014, 4 pages.

Oliveira et al., "Renal Denervation Normalizes Pressure and Baroreceptor Reflex in High Renin Hypertension in Conscious Rats," Hypertension, Supplement II, vol. 19, No. 2, Feb. 1992, pages II-17 to II-21.

Ong et al. "Prevalence, Awareness, Treatment, and Control of Hypertension Among United States Adults 1999-2004." Hypertension, vol. 49, Issue 1, Jan. 1, 2007, pp. 69-75 (originally published online Dec. 11, 2006).

Ormiston et al., "First-in-Human Use of the OneShot™ Renal Denervation System from Covidien," EuroIntervention, vol. 8, Jan. 2013, pp. 1090-1094.

Ormiston et al., "Renal Denervation for Resistant Hypertension Using an Irrigated Radiofrequency Balloon: 12-month Results from the Renal Hypertension Ablation System (RHAS) Trial," EuroIntervention, vol. 9, May 2013, pp. 70-74.

Oz, "Pressure Relief," TIME, Jan. 9, 2012, 2 pp. Retrieved from the Internet: www.time.come/time/printout/0,8816,21 03278,00.html.

Page et al., "The Effect of Renal Denervation on the Level of Arterial Blood Pressure and Renal Function in Essential Hypertension," The Journal of Clinical Investigation, Sep. 12, 1934, vol. 14, No. 1, pp. 27-30.

Papademetriou et al., "Catheter-Based Renal Denervation for Resistant Hypertension: 12-Month Results of the EnligHTN I First-in-Human Study Using a Multielectrode Ablation System," Hypertension, vol. 64, Issue 3, Sep. 2014, pp. 565-572.

Papademetriou et al., "Renal Denervation and Symplicity HTN-3: "Dubium Sapientiae Initium" (Doubt Is the Beginning of Wisdom)," Circulation Research, vol. 115, Issue 2, Jul. 7, 2014, pp. 211-214.

Papademetriou et al., "Renal Nerve Ablation for Resistant Hypertension: How Did We Get Here, Present Status, and Future Directions," Circulation, vol. 129, Issue 13, Apr. 1, 2014, pp. 1440-1451.

Papademetriou et al., "Renal Sympathetic Denervation for the Treatment of Difficult-to-Control or Resistant Hypertension," International Journal of Hypertension, Article ID 196518, Mar. 30, 2011, 8 pp.

Pedersen, "TCT 2012: Renal Denervation Device Makers Play Show and Tell," Medical Device Daily, Oct. 26, 2012, 2 pp., Retrieved from the Internet: URL: http://www.medicaldevicedaily.com/servlet/com.accumedia.web.Dispatcher?next=bioWorldHeadlines_article&forceid=80880.

Peet, "Hypertension and its Surgical Treatment by Bilateral Supradiaphragmatic Splanchnicectomy," The American Journal of Surgery, vol. 75, Issue 1, Jan. 1, 1948, pp. 48-68.

Pokushalov et al., "A Randomized Comparison of Pulmonary Vein Isolation With Versus Without Concomitant Renal Artery Denervation in Patients With Refractory Symptomatic Atrial Fibrillation and Resistant Hypertension." Journal of the American College of Cardiology, vol. 60, No. 13, Sep. 25, 2012, pp. 1163-1170.

(56) References Cited

OTHER PUBLICATIONS

Prochnau et al., "Catheter-Based Renal Denervation for Drug-Resistant Hypertension by Using a Standard Electrophysiology Catheter," EuroIntervention, Jan. 2012, vol. 7, No. 9, pp. 1077-1080.
Purerfellner et al., "Incidence, Management, and Outcome in Significant Pulmonary Vein Stenosis Complicating Ablation for Atrial Fibrillation," The American Journal of Cardiology, vol. 93, Issue 11, Jun. 1, 2004, pp. 1428-1431.
Purerfellner et al., "Pulmonary Vein Stenosis Following Catheter Ablation of Atrial Fibrillation," Current Opinion in Cardiology, vol. 20, Issue 6, Nov. 2005, pp. 484-490.
Schauerte et al. "Catheter Ablation of Cardiac Autonomic Nerves for Prevention of Vagal Atrial Fibrillation," Circulation, vol. 102, Issue 22, Nov. 28, 2000, pp. 2774-2780.
Schlaich et al., "Renal Denervation in Human Hypertension: Mechanisms, Current Findings, and Future Prospects," Current Hypertension Reports, vol. 14, Jun. 2012, pp. 247-253.
Schmid et al., "Does Renal Artery Supply Indicate Treatment Success of Renal Denervation," Cardiovascular and Interventional Radiology, vol. 36, No. 4, Apr. 2013, pp. 987-991.
Schmieder et al., "Updated ESH Position Paper on Interventional Therapy of Resistant Hypertension," EuroIntervention, vol. 9, Supplement R, May 2013, pp. R58-R66.
Schneider, "Endovascular Skills—Guidewire and Catheter Skills for Endovascular Surgery," Second Edition Revised and Expanded, 2003, 10 pp. (Applicant points out, in accordance with MPEP 609.04(a), that the year of publication, 2003, is sufficiently earlier than the effective U.S. filing date, so that the particular month of publication is not in issue).
Sievert, "Novelty Award EuroPCR 2010," Euro PCR, 2010, 15 pp. (Applicant points out, in accordance with MPEP 609.04(a), that the year of publication, 2010, is sufficiently earlier than the effective U.S. filing date, so that the particular month of publication is not in issue).
Solis-Herruzo et al., "Effects of Lumbar Sympathetic Block on Kidney Function in Cirrhotic Patients with Hepatorenal Syndrome," Journal of Hepatology, vol. 5, Issue 2, Jan. 1, 1987, pp. 167-173.
Stella, et al., "Effects of Reversible Renal Denervation on Haemodynamic and Excretory Functions on the Ipsilateral and Contralateral Kidney in the Cat," Journal of Hypertension, vol. 4, No. 2, Apr. 1, 1986, pp. 181-188.
Stouffer et al., "Catheter-Based Renal Denervation in the Treatment of Resistant Hypertension," Journal of Molecular and Cellular Cardiology, vol. 62, Sep. 1, 2013, pp. 18-23.
Swartz et al., "Radiofrequency Endocardial Catheter Ablation of Accessory Atrioventricular Pathway Atrial Insertion Sites," Circulation, Vo. 87, No. 2, Feb. 1993, pp. 487-499.
Tsao et al. "Evaluation of Pulmonary Vein Stenosis after Catheter Ablation of Atrial Fibrillation," Cardiac Electrophysiology Review, vol. 6, No. 4, Dec. 2002, pp. 397-400.
U.S. Appl. No. 60/442,970, by Gelfand et al., filed Jan. 29, 2003.
Uchida et al., "Effect of Radiofrequency Catheter Ablation on Parasympathetic Denervation: A Comparison of Three Different Ablation Sites," Pacing and Clinical Electrophysiology: PACE, vol. 21, Issue 11, Nov. 1998, pp. 2517-2521.
Verloop et al., "Renal Denervation: A New Treatment Option in Resistant Arterial Hypertension," Netherlands Heart Journal, vol. 21, Nov. 30, 2012, pp. 95-98, Retrieved from the Internet: URL: http://www.ncbi.nlm.nih.gov/pmc/articles/PMC3547427.
Weinstock et al., "Renal Denervation Prevents Sodium Retention and Hypertension in Salt Sensitive Rabbits with Genetic Baroreflex Impairment," Clinical Science, vol. 90, Issue 4, Apr. 1996, pp. 287-293.
Wilcox, "Scientific Basis Behind Renal Denervation for the Control of Hypertension," ICI 2012, Medtronic, Inc., Dec. 5-6, 2012. 38 pp.
Wittkampf et al., "Control of Radiofrequency Lesion Size by Power Regulation," Circulation, vol. 80, No. 4, Oct. 1989, pp. 962-968.
Worthley et al., "Safety and Efficacy of a Multi-Electrode Renal Sympathetic Denervation System in Resistant Hypertension: The EnligHTN I Trial," European Heart Journal, vol. 34, Jul. 2013, pp. 2132-2140.
Worthley, "The St. Jude Renal Denervation System Technology and Clinical Review," The University of Adelaide Australia, 2012, 24 pp. (Applicant points out, in accordance with MPEP 609.04(a), that the year of publication, 2012, is sufficiently earlier than the effective U.S. filing date, so that the particular month of publication is not in issue).
Zheng et al., "Comparison of the Temperature Profile and Pathological Effect at Unipolar, Bipolar and Phased Radiofrequency Current Configurations," Journal of Interventional Cardiac Electrophysiology, vol. 5, Dec. 2001, pp. 401-410.
Zuern et al., "Impaired Cardiac Baroflex Sensitivity Predicts Response to Renal Sympathetic Denervation in Patients with Resistant Hypertension," Journal of the American College of Cardiology, vol. 62, No. 22, Dec. 3, 2013, pp. 2124-2130.
Office Action, and translation thereof, from counterpart Japanese Application No. 2020-560877 dated Nov. 7, 2022, 8 pp.
Communication pursuant to Article 94(3) EPC from counterpart European Application No. 19704912.5 dated Feb. 1, 2024, 5 pp.
Response to Communication pursuant to Article 94(3) EPC dated Feb. 1, 2024, from counterpart European Application No. 19704912.5 filed May 2, 2024, 11 pp.

\* cited by examiner

SYSTEMS, DEVICES, AND METHODS FOR ASSESSING EFFICACY OF RENAL NEUROMODULATION THERAPY

CROSS-REFERENCE TO RELATED APPLICATION(S)

The present application claims the benefit of U.S. Provisional Patent Application No. 62/621,304, filed Jan. 24, 2018, the disclosure of which is incorporated herein by reference in its entirety.

TECHNICAL FIELD

The present technology is related to neuromodulation. In particular, various embodiments of the present technology are related to systems and methods for measuring a diameter of a blood vessel and modifying a parameter of neuromodulation therapy performed in the blood vessel based on the measured vessel diameter.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic over-activation of the SNS, however, is a common maladaptive response that can drive the progression of many disease states. Excessive activation of the renal SNS in particular has been identified experimentally and in humans as a likely contributor to the complex pathophysiology of arrhythmias, hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome, (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

DETAILED DESCRIPTION

Figure 1A:
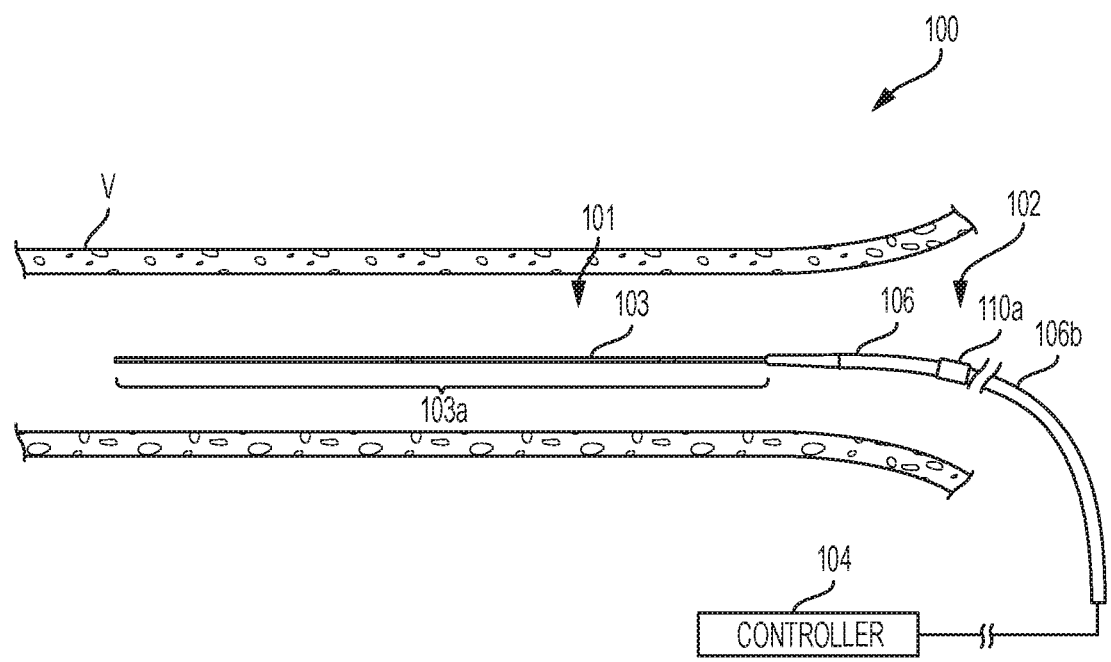
FIG. 1A is a partially schematic side view of a neuromodulation system with a distal portion of a guidewire positioned within a blood vessel of a human patient in accordance with embodiments of the present technology.

Systems and methods in accordance with embodiments of the present technology are directed to obtaining measurements related to a dimension of a renal blood vessel before a neuromodulation procedure, such as a renal denervation procedure, to periprocedurally assess the likely efficacy of the neuromodulation procedure. The disclosed techniques can be used, for example, to assess a particular patient's likelihood of deriving a therapeutic benefit from delivered neuromodulation energy.

Recent research suggests that the diameter of a renal blood vessel may be correlated to the efficacy (e.g., a resulting drop in blood pressure, reduction in risks associated with cardiovascular disease, improvement in heart failure status, reduction in arrhythmias, etc.) of a renal denervation procedure subsequently performed in that vessel. More specifically, renal denervation may be more effective in renal blood vessels having a comparatively smaller diameter. The reasons for improved efficacy may be due to any number of factors. For example, renal nerves tend to be further from the vessel wall in larger diameter renal blood vessels and, contrariwise, closer to the vessel wall in smaller diameter renal blood vessels. Moreover, smaller vessels may permit greater applanation pressure of a neuromodulation catheter—thereby resulting in better contact between neuromodulation electrodes on the catheter and the vessel wall. Furthermore, the net proportion of a vessel circumference impacted by a single lesion from an individual neuromodulation electrode may be greater in a smaller vessel. Regardless of the specific reason for improved efficacy, measuring the diameter of a renal blood vessel (or a related value) before a neuromodulation procedure is performed in that particular vessel is expected to provide periprocedural information about the likely success (or lack thereof) of the neuromodulation procedure. Moreover, such information can be used to modify or adjust a parameter of the neuromodulation procedure—such as power, time, location, and/or other characteristic of energy delivered during the neuromodulation procedure—to improve the likelihood that the neuromodulation procedure will be successful.

Currently, there are only limited means available for a practitioner performing a neuromodulation procedure to know whether and/or where the procedure is likely to be successful. Moreover, current techniques for measuring the diameter of renal blood vessels—e.g., quantitative angiography and intravascular ultrasound—require additional devices and procedures, and can be slow, expensive, and relatively inaccurate.

In contrast with conventional techniques, in several of the embodiments described below, a neuromodulation system can include a neuromodulation catheter configured to both (i) detect one or more measurements related to a dimension of a renal blood vessel at or near a target site in the vessel and (ii) deliver therapeutic neuromodulation at the target site. A controller can receive the one or more measurements and accurately estimate a diameter of the renal blood vessel at or near the target site. Based, at least in part, on the diameter, an operator of the neuromodulation system and/or the controller can (i) assess the likely efficacy of delivering therapeutic neuromodulation at the target site, (ii) adjust one or more parameters of the therapeutic neuromodulation to be delivered at the target site, and/or (iii) reposition the neuromodulation catheter to a new target site. Accordingly, systems configured in accordance with the present technology are expected to improve the efficacy of a neuromodulation procedure by detecting a simple pre-neuromodulation measurement of the renal blood vessel in which the neuromodulation is performed—without the need for expensive and untimely additional measurements using separate, conventional, measurement systems.

Specific details of several embodiments of the present technology are described herein with reference to FIGS. 1A-13. Although many of the embodiments are described with respect to devices, systems, and methods for intravascular renal neuromodulation, other applications and other embodiments in addition to those described herein are within the scope of the present technology. For example, at least some embodiments of the present technology may be useful for extravascular neuromodulation, intravascular non-renal neuromodulation, and/or use in therapies other than neuromodulation. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of a neuromodulation catheter). The terms, "distal" and "distally" refer to a position distant from or in a direction away from a clinician or a clinician's control device along the length of device. The terms "proximal" and "proximally" refer to a position near or in a direction toward a clinician or a clinician's control device along the length of device. The headings provided herein are for convenience only and should not be construed as limiting the subject matter disclosed.

I. SELECTED EMBODIMENTS OF NEUROMODULATION CATHETERS AND SYSTEMS

Figure 1B:
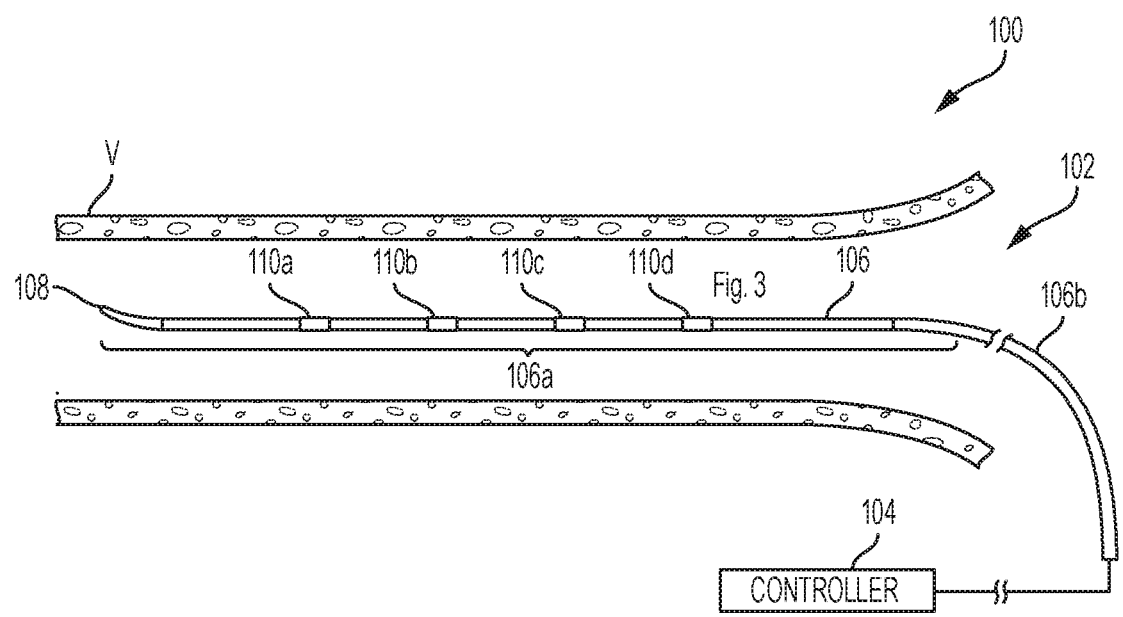
FIGS. 1B and 1C are partially schematic side views of the neuromodulation system shown in FIG. 1A with a distal portion of a neuromodulation catheter in a first state and a second state, respectively, within the blood vessel of the human patient in accordance with embodiments of the present technology.
Figure 1C:
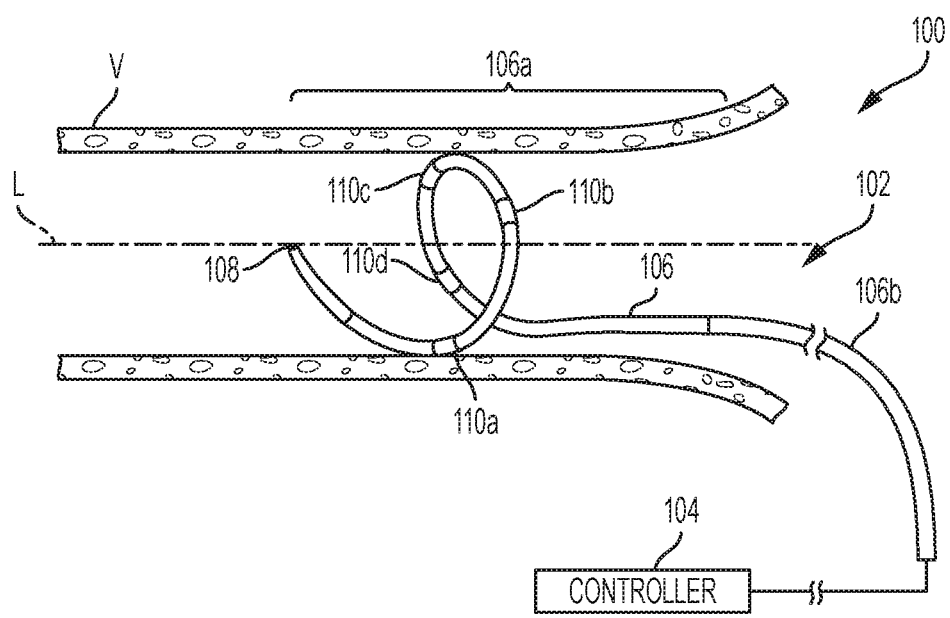

FIGS. 1A-1C are partially schematic side views of a neuromodulation system 100 ("system 100") configured in accordance with an embodiment of the present technology and shown in different arrangements while positioned at a target site within a blood vessel V (e.g., a renal artery) of a human patient. The system 100 includes a guidewire 101 (only visible in FIG. 1A) and a neuromodulation catheter 102 that can be advanced over the guidewire 101 to the target site within the blood vessel V. In other embodiments, the neuromodulation catheter 102 can be configured for delivery to the target site via other methods (e.g., via a guide catheter, via sheath retraction, via a pull-wire, etc.).

The neuromodulation catheter 102 is configured to perform neuromodulation therapy at the target site to, for example, ablate nerves proximate the wall of the blood vessel V. As discussed in greater detail below, the neuromodulation catheter 102 is further configured to detect one or more measurements related to a dimension (e.g., a diameter, a cross-sectional area, a circumference, a segmental volume, etc.) of the blood vessel V before neuromodulation therapy to assess the likely efficacy of subsequent neuromodulation therapy performed at the target site. The system 100 further includes one or more controllers 104 communicatively coupled to the neuromodulation catheter 102 via a wired or wireless communication link.

Referring to FIG. 1A, the guidewire 101 includes an elongated member 103 having a distal portion 103a configured to be positioned at the target site within the blood vessel V and a proximal portion (not visible) that extends outside of the patient to a handle (not shown) or other feature(s) that allow an operator to manipulate the distal portion 103a to the desired position/orientation. The elongated member 103 can be sized to be slidably positioned within a lumen of the neuromodulation catheter 102. Additionally, the elongated member 103 can have a uniform stiffness along its length, or can have a stiffness that varies along its length. In other embodiments, the elongated member 103 may comprise other suitable components and/or configurations.

As best shown in FIG. 1B, the neuromodulation catheter 102 includes an elongated shaft 106 configured to be slidably delivered over the guidewire 101. The elongated shaft 106 has a distal portion 106a configured to be intravascularly positioned at the target site within the blood vessel V and a proximal portion 106b extending outside of the patient to a handle (not shown) or other features that allow an operator to manipulate the distal portion 106a of the elongated shaft 106. As shown in FIGS. 1B and 1C, for example, the neuromodulation catheter 102 is transformable between a first state or arrangement in which the distal portion 106a of the elongated shaft 106 is at least generally straight and in a low-profile delivery arrangement (FIG. 1B), and a second (e.g., deployed, expanded, etc.) state or arrangement in which the distal portion 106a is transformed or otherwise expanded to a spiral/helical shape (FIG. 1C).

Referring to FIGS. 1B and 1C together, the neuromodulation catheter 102 includes a plurality of energy delivery elements, such as electrodes 110 spaced along the distal portion 106a of the elongated shaft 106 and a distal tip 108 (e.g., an atraumatic tip). In the illustrated embodiment, the neuromodulation catheter 102 includes four electrodes 110 (identified individually as first through fourth electrodes 110a-110d, respectively). In other embodiments, however, the neuromodulation catheter 102 may include one, two, three, or more than four electrodes 110, and/or may include different energy delivery elements. The electrodes 110 are configured to deliver neuromodulation energy to the target site to modulate or ablate nerves (e.g., renal nerves) proximate to the target site. In other embodiments, the neuromodulation catheter 102 can include electrodes, transducers, or other elements to deliver energy to modulate nerves using other suitable neuromodulation modalities, such as pulsed electrical energy, microwave energy, optical energy, ultrasound energy (e.g., intravascularly delivered ultrasound and/or high-intensity focused ultrasound (HIFU)), direct heat energy, radiation (e.g., infrared, visible, and/or gamma radiation), and/or other suitable types of energy. In certain embodiments, the neuromodulation catheter 102 may be configured for cryotherapeutic treatment, and can apply cryogenic cooling to the vessel V with a refrigerant (e.g., via a balloon catheter that circulates the refrigerant).

The dimensions (e.g., outer diameter and length) of the distal portion 106a of the elongated shaft 106 (e.g., the portion that takes on the spiral/helical shape in the second state illustrated in FIG. 1C) can be selected to accommodate the vessels or other body lumens in which the distal portion 106a is designed to be delivered. For example, when in the second state, the axial length of the distal portion 106a of the elongated shaft 106 may be selected to be no longer than a patient's renal artery (e.g., typically less than 7 cm), and have a diameter that accommodates the inner diameter of a typical renal artery (e.g., about 2-10 mm). In other embodiments, the distal portion 106a of the elongated shaft 106 can have other dimensions depending on the body lumen within which it is configured to be deployed. Regardless of the selected dimensions of the distal portion 106a, in some embodiments, one or more dimensions of the distal portion 106a are known prior to performing a neuromodulation procedure with the neuromodulation catheter 102. As described in greater detail below, in some embodiments, the known dimensions can be used to calculate other (e.g., variable, unknown, non-constant, etc.) dimensions of the distal portion 106a such as a diameter of the distal portion 106a in the spiral/helical second state. In further embodiments, the distal portion 106a of the elongated shaft 106 can have other suitable shapes (e.g., semi-circular, curved, straight, etc.), and/or the neuromodulation catheter 102 can include multiple support members configured to carry one or more electrodes 110. The distal portion 106a of the elongated shaft 106 may also be designed to apply a desired outward radial force to a vessel when expanded to the spiral/helical second state to place one or more of the electrodes 110 in contact with the vessel wall.

In some embodiments, the system 100 includes a console (not shown). The controller 104 may be separated from the console or may be integrated with the console. The controller 104 can be configured to initiate, terminate, and/or adjust operation of one or more components (e.g., the electrodes 110) of the neuromodulation catheter 102 directly and/or via the console. For example, as described in greater detail below, the controller 104 may be configured to continuously or intermittently monitor the impedance between each of the electrodes 110. The console can be configured to communicate with the neuromodulation catheter 102 via a wireless and/or wired communication link. For example, in some embodiments the console can include an access port for receiving a wired connection to the neuromodulation catheter 102. The console can be configured to control, monitor, supply, and/or otherwise support operation of the neuromodulation catheter 102. The console can further be configured to generate a selected form and/or magnitude of energy for delivery to tissue at the target site via the electrodes 110, and therefore the console may have different configurations depending on the treatment modality of the neuromodulation catheter 102. For example, the console can include an energy generator (not shown) configured to generate RF energy. Further, the console can be configured to provide feedback to an operator before, during, and/or after a neuromodulation procedure such as, for example, a determined diameter of the blood vessel V and/or a likely efficacy of a neuromodulation procedure performed at the target site.

Although the embodiment of the neuromodulation catheter 102 shown in FIGS. 1A-1C has a spiral/helically-shaped configuration, in other embodiments, the neuromodulation catheter 102 can have other suitable shapes, sizes, and/or configurations. Other suitable devices and technologies are described in, for example, U.S. Pat. Nos. 8,777,942; 9,084,610; 9,060,755; 8,998,894; PCT Application No. PCT/US2011/057754, filed Oct. 25, 2011; and U.S. Pat. No. 8,888,773. All of the foregoing applications are incorporated herein by reference in their entireties. Another non-limiting example of a device includes the Symplicity Spyral™ multielectrode RF ablation catheter.

II. SELECTED EMBODIMENTS OF NEUROMODULATION CATHETERS HAVING MEASURING ELEMENTS FOR DETERMINING A DIMENSION OF A BLOOD VESSEL

As described above, it is expected that neuromodulation therapy is more likely to be successful or effective (e.g., causing a desired degree of ablation of targeted nerves and/or ablating a sufficient volume of targeted nerves) when performed in blood vessels having a smaller diameter, or in relatively smaller sections of the same blood vessel. Accordingly, it may be advantageous to measure a dimension (e.g., a diameter) of a blood vessel of a patient in order to, correlatively, determine a likely efficacy of neuromodulation therapy performed in that vessel and/or to modify one or more parameters of the neuromodulation therapy. In general, as described in detail below, the system 100 of the present technology includes at least one measuring element configured to detect (e.g., obtain, make, etc.) one or more measurements related to a dimension of a blood vessel before delivery of neuromodulation energy.

For example, in some embodiments, the measuring element can comprise one or more of the electrodes 110 at the distal portion 106a of the elongated shaft 106 of the neuromodulation catheter 102. In such embodiments, the system 100 can be configured to measure impedance between two or more of the electrodes 110 before neuromodulation energy is delivered via the electrodes 110. The detected impedance measurements can be transmitted to the controller 104 and/or another device external to the patient. The controller 104 can be configured to receive and store the detected impedance measurements and determine a dimension (e.g., a diameter) of the blood vessel V based, at least in part, on one or more of the detected impedance measurements.

More particularly, in some embodiments, signals (e.g., low power electric signals) may be sent between one or more pairs of the electrodes 110 to measure impedance between the electrodes 110. In certain embodiments, the impedance between combinations of two different electrodes may be measured. For example, signals may be sent between (i) the first electrode 110a and the second electrode 110b, (ii) the first electrode 110a and the third electrode 110c, (iii) the first electrode 110a and the fourth electrode 110d, (iv) the second electrode 110b and the third electrode 110c, (v) the second electrode 110b and the fourth electrode 110d, and (vi) the third electrode 110c and the fourth electrode 110d. In some embodiments, impedance measurements may be obtained for less than every combination of pairs of the electrodes 110 (e.g., a single impedance measurement between the first electrode 110a and the fourth electrode 110d).

Regardless of the combination(s) of electrodes 110 that are used to measure impedance, the obtained impedance measurements may be stored at the controller 104 and processed to determine a dimension of the blood vessel V near the electrodes 110 (e.g., near the target site). For example, in some embodiments, the dimension of the blood vessel V can be estimated using the cylindrical equation:

$$A = \frac{\rho L^2}{R} \quad (1)$$

As is well known in the art, the cylindrical equation (1) provides that the cross-sectional area A of a cylinder of relatively constant diameter filled with a material of constant resistivity p is proportional to the impedance R measured over a distance L. The resistivity p of the blood in the blood vessel V may be directly measured or estimated by applying one or more pre-determined correction coefficients to the cylindrical equation (1). Accordingly, based on a known longitudinal distance L between selected electrodes 110, the cross-sectional area A (and hence a diameter of the blood vessel V) can be estimated.

In general, impedance measurements and/or related values (e.g., the corresponding longitudinal distances between electrodes, the corresponding diameter of the vessel, etc.) can be averaged and/or otherwise combined to provide a relatively accurate estimate of the diameter or another dimension (e.g., circumference) of the blood vessel V. In certain embodiments, impedance measurements detected by the electrodes 110 can be used to determine an actual (e.g., absolute) dimension of the blood vessel V while, in other embodiments, impedance measurements can be compared to a baseline measurement to determine a relative difference in the dimension of the blood vessel V (e.g., from a first location to a second location within the vessel).

One advantage of using the electrodes 110 to detect a measurement related to a dimension of the blood vessel V is that no physical modifications need to be made to the neuromodulation catheter 102. That is, the same electrodes 110 that deliver neuromodulation energy may be used to determine the diameter of the target blood vessel V if the resistivity of the blood in the blood vessel V is known or can be estimated.

Figure 2:
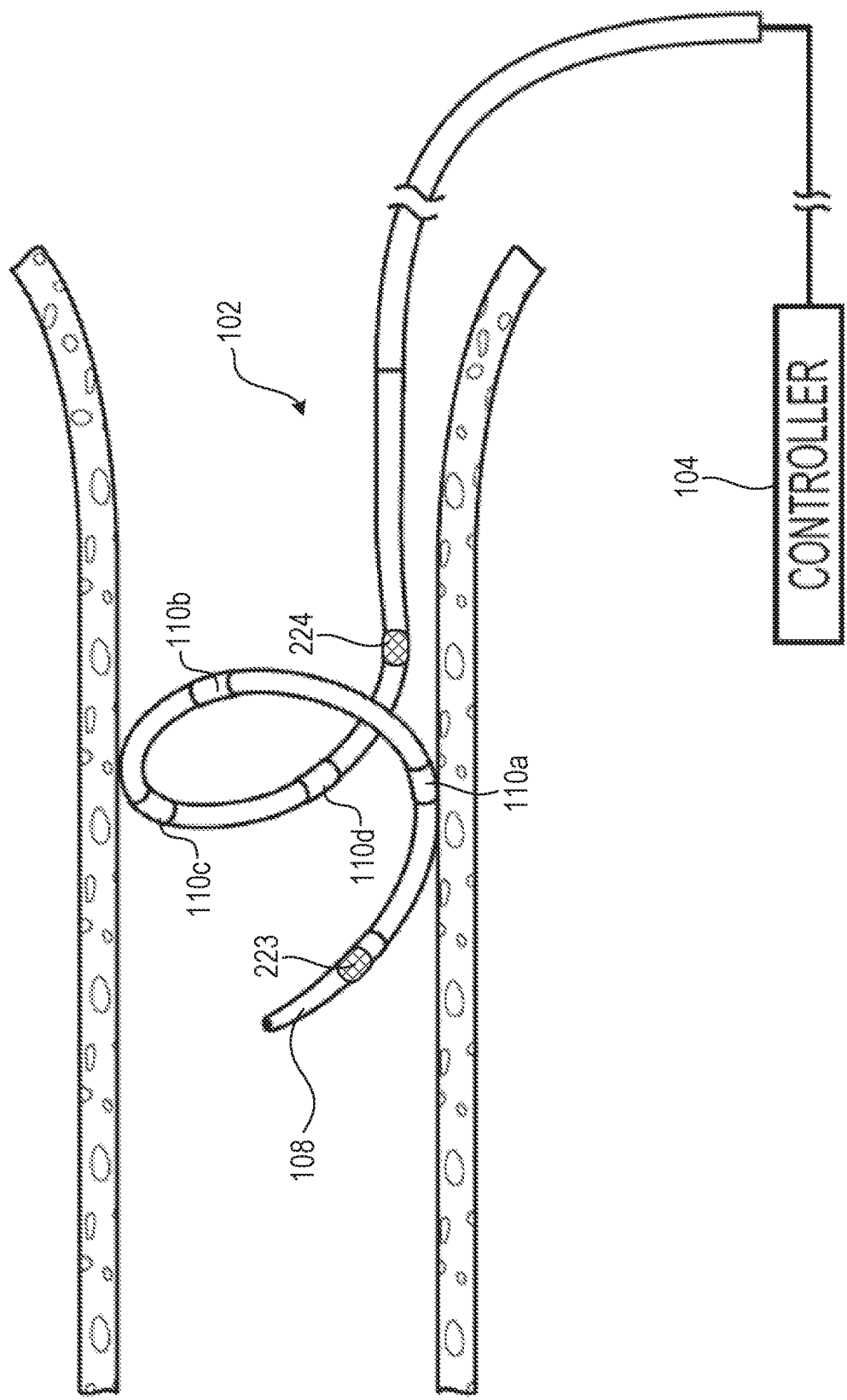
FIG. 2 is a partially schematic side view of the neuromodulation system shown in FIG. 1C with a distance sensor configured in accordance with embodiments of the present technology.

In certain embodiments, the measuring element of the system 100 may comprise a separate component positioned at the distal portion of the neuromodulation catheter 102. FIG. 2, for example, is a partially schematic side view of the neuromodulation system shown in FIG. 1C (e.g., in the second state) and including a distance sensor (e.g., a proximity sensor). The distance sensor can be configured to detect a distance between a first portion of the neuromodulation catheter 102, such as the distal tip 108, and a second, more proximal portion of the neuromodulation catheter 102. For example, in the illustrated embodiment, the distance sensor includes a first sensing component 223 on the distal tip 108 and a second sensing component 224 on the distal portion of the neuromodulation catheter 102 and positioned proximal to the fourth electrode 110d. In some embodiments, the distance sensor is a capacitive distance sensor, a Hall effect distance sensor, a piezoelectric distance sensor, a magnetic distance sensor, and/or another type of distance sensor configured to measure a distance between the first and second sensing components 223, 224 ("sensing components 223, 224"). The detected distance between the sensing components 223, 224 can be used to determine a dimension (e.g., diameter) of the blood vessel V based on known dimensions of the neuromodulation catheter 102.

In particular, the detected distance between the sensing components 223, 224 can be used to determine the diameter of the blood vessel V since, for example, the longitudinal distance between the sensing components will vary in conformance with the diameter of the blood vessel V (e.g., the longitudinal distance will be greater when the blood vessel V has a smaller diameter and the distal portion of the neuromodulation catheter 102 is not fully radially expanded). More specifically, in some embodiments, the longitudinal distance between the sensing components 223, 224 can be used to determine an angle of rotation of the distal portion of the neuromodulation catheter 102 when the neuromodulation catheter 102 is in the second (expanded) state. Based on known dimensions of the neuromodulation catheter 102, the angle of rotation can be used to calculate the diameter of the distal portion of the neuromodulation catheter 102 that apposes the inner wall of the blood vessel V. Accordingly, the determined diameter of the distal portion of the neuromodulation catheter 102 can be used to estimate the diameter of the blood vessel V.

In other embodiments, the sensing components 223, 224 may be positioned differently with respect to the neuromodulation catheter 102. For example, the second sensing component 224 may be positioned further distally or proximally with respect to the neuromodulation catheter 102 (e.g., adjacent to one of the electrodes 110) and/or the first sensing component 223 may be positioned proximal to the distal tip 108. In the illustrated embodiment, the sensing components 223, 224 are positioned on the exterior of the neuromodulation catheter 102. In other embodiments, however, the sensing components 223, 224 may be positioned fully within (i.e., internal to) or partially within the neuromodulation catheter 102. In certain embodiments, the system 100 can include more than one distance sensor and/or one or more distance measurements may be averaged or otherwise combined to estimate a dimension of the blood vessel V. Moreover, the sensing components 223, 224 can be coupled to the controller 104 and/or other components of the system 100 via one or more wires extending through the neuromodulation catheter 102, or the sensing components 223, 224 can be wirelessly coupled to the controller 104 and/or other components of the system 100.

Figure 3:
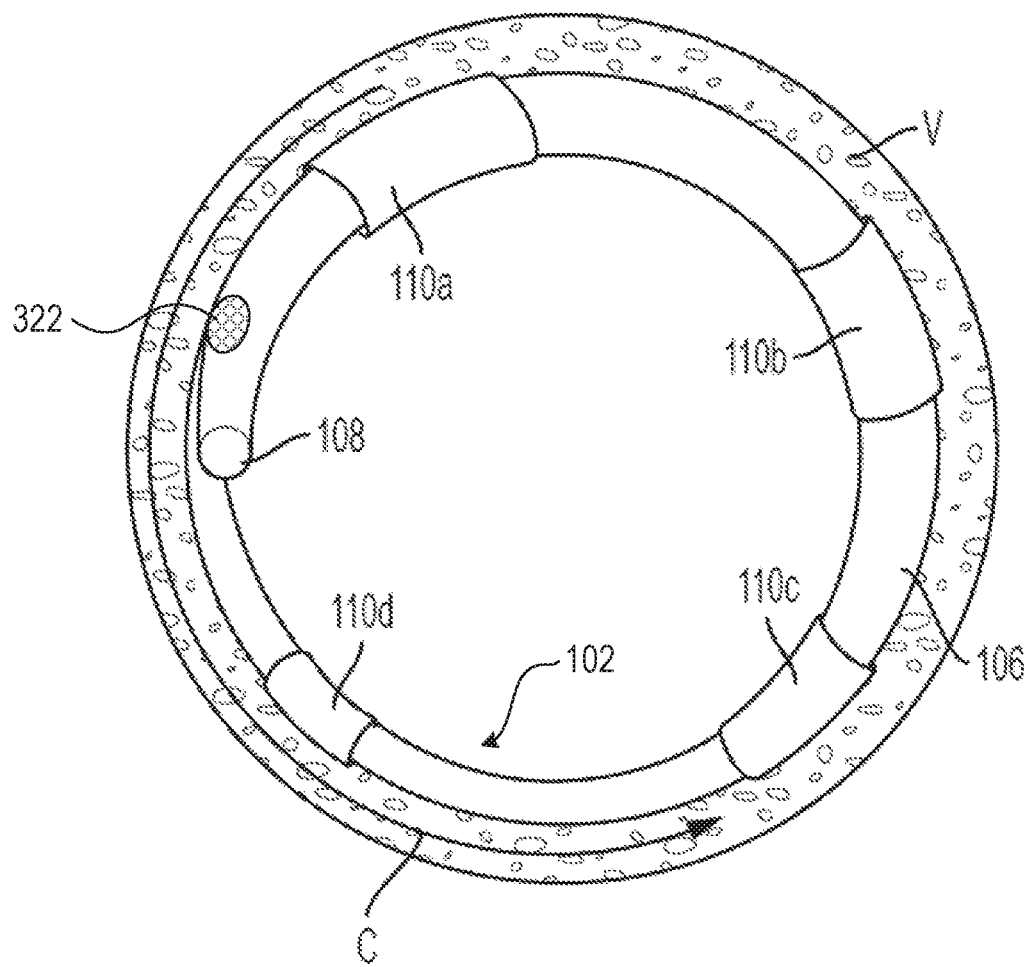
FIG. 3 is a front view of the neuromodulation catheter shown in FIG. 1C looking proximally down a longitudinal axis of the blood vessel of the human patient.

FIG. 3 illustrates another embodiment of a measuring element positioned at the distal portion of the neuromodulation catheter 102. In particular, FIG. 3 is a front view of the distal portion of the neuromodulation catheter 102 in the second state shown in FIG. 1C, and looking down a longitudinal axis L (shown in FIG. 1C) of the blood vessel V in the proximal direction. As shown in FIG. 3, the system 100 can include a distance sensor 322 positioned at the distal tip 108 of the neuromodulation catheter. In other embodiments, the distance sensor 322 may be positioned elsewhere on the distal portion of the neuromodulation catheter 102. The distance sensor 322 can be an odometer-type sensor (e.g., a wheel, track ball, other rotatable component, etc.) configured to measure a circumference (or other dimension) of the blood vessel V as the distal portion of the neuromodulation catheter 102 is rotated within the blood vessel V. For example, the system 100 can be configured to automatically (e.g., via a motor external to the patient) rotate the distal portion of the neuromodulation catheter 102 in the direction of arrow C such that the distance sensor 322 passes completely around a circumference of the blood vessel V (e.g., one full rotation). The detected circumference of the blood vessel V can be easily used to determine the diameter of the blood vessel V.

In other embodiments, the measuring element of the system 100 can comprise other components suitable for detecting a measurement related to a dimension of the blood vessel V. For example, in some embodiments, a balloon or other inflatable component can be positioned at least partially at the distal portion of the neuromodulation catheter 102. For example, the balloon can be (i) positioned on the exterior of the neuromodulation catheter 102, (ii) have at least one fixed dimension (e.g., a fixed longitudinal length), and (iii) can be inflated with a measured (e.g., known) volume or inflation pressure. Thus, the diameter of the blood vessel V can be estimated once the balloon is inflated to be in contact with the inner wall of the blood vessel V. In some embodiments, the balloon may have one or more electrodes configured to detect when the balloon contacts the inner wall of the blood vessel V. In some such embodiments, the electrodes on the balloon may also be configured to deliver neuromodulation energy. In other embodiments, a pressure inside the balloon can be measured and used to detect when the balloon contacts the inner wall of the blood vessel V. For example, a sudden increase in the pressure of the balloon could indicate that the balloon is in apposition with the inner wall of the blood vessel V.

In other embodiments, the measuring element of the system 100 can comprise one or more wires or other electrical elements positioned at the distal portion of the neuromodulation catheter 102 and having a variable resistance that changes based on how much the electrical elements are bent. In some such embodiments, for example, the resistance of the electrical elements can be used to determine (e.g., can be correlated to) the diameter of the distal portion of the neuromodulation catheter 102. Specifically, the change in resistance can be directly correlated to the curvature of the neuromodulation catheter 102, which can be used to determine the diameter of the blood vessel V, as set forth in detail above. Thus, the diameter of the blood vessel V can be estimated based on the resistance of the electrical elements.

In yet other embodiments, the measuring element 100 can comprise standard imaging systems and/or components used in well-known imaging techniques such as, for example, fluoroscopy, magnetic resonance imaging (MRI), intravascular ultrasound (IVUS), etc.

Each of the embodiments described are expected to facilitate measurement(s) related to a dimension of the blood vessel V via the neuromodulation catheter 102. Such measurements can be used to determine or estimate the diameter of the blood vessel V near a target site in the blood vessel V and, correlatively, the likely efficacy of neuromodulation therapy subsequently performed at the target site. Thus, embodiments of the present technology are expected to quickly and cheaply determine the likely efficacy of neuromodulation therapy since the same device may be used to both measure a dimension of a target blood vessel and deliver neuromodulation energy to target nerves adjacent that same vessel. As described in further detail below, the present technology is also expected to improve the efficacy of neuromodulation therapy by permitting (i) customization of a neuromodulation energy delivery profile and/or (ii) improved target site selection.

III. SELECTED METHODS FOR ASSESSING THE LIKELY EFFICACY OF NEUROMODULATION THERAPY AND/OR MODIFYING ONE OR MORE PARAMETERS OF NEUROMODULATION THERAPY

Figure 4:
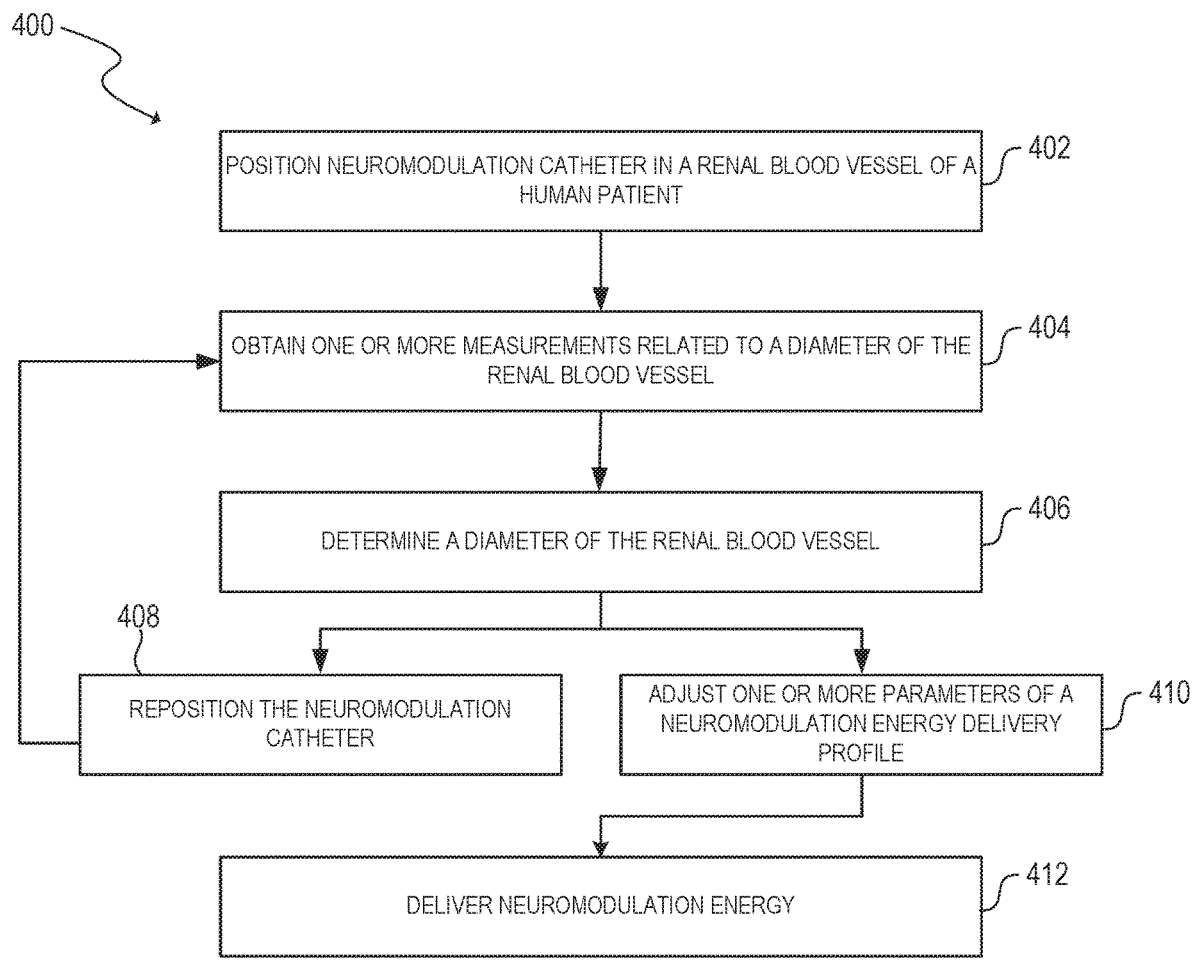
FIG. 4 is a flow diagram of a process or method for evaluating the likely efficacy of neuromodulation therapy and/or modifying one or more parameters of neuromodulation therapy in accordance with embodiments of the present technology.

FIG. 4 is a flow diagram of a method or process 400 for evaluating the likely efficacy of neuromodulation therapy and/or modifying one or more parameters of neuromodulation therapy in accordance with embodiments of the present technology. The method 400 can be implemented using the system 100 described above with reference to FIGS. 1A-3 and/or using other suitable systems. For example, the neuromodulation catheter 102 and/or the controller 104 can be used to perform the various steps of the method 400. Accordingly, for sake of illustration, some features of the method 400 will be described in the context of the embodiments shown in FIGS. 1A-3.

Beginning at block 402, the method 400 includes positioning the neuromodulation catheter 102 at a target site within the blood vessel V of the human patient. In some embodiments, positioning the neuromodulation catheter 102 includes (i) positioning the guidewire 101 along a portion of the blood vessel V proximate the target site (FIG. 1A), (ii) advancing the neuromodulation catheter 102 over the guidewire 101 to the target site (FIG. 1B), and (iii) transforming or otherwise expanding the distal portion of the neuromodulation catheter 102 to the spiral/helical shape in which the electrodes 110 contact the wall of the blood vessel V (FIG. 1C).

At block 404, the method 400 includes obtaining one or more measurements related to or corresponding to a dimension (e.g., a diameter, a circumference, etc.) of the blood vessel V near the target site by, for example, using the measuring element of the neuromodulation catheter 102. For example, as described in detail above, the measurements can include one or more of the following: impedance measurement(s) between two or more of the electrodes 110; a distance between spaced apart portions of the neuromodulation catheter 102; a distance between two or more of the electrodes 110; an angle of rotation of the distal portion of the neuromodulation catheter 102; a volume of an inflatable balloon; etc. More particularly, in certain embodiments in which the measuring element comprises the electrodes 110, the controller 104 can be configured to (i) control the electrodes 110 to generate and detect one or more signals that propagate through the blood vessel V and (ii) determine one or more impedance values between two or more of electrodes 110 that are related to the dimension of the blood vessel V. In other embodiments, where the measuring element comprises a distance sensor (FIGS. 2 and 3), the controller 104 can be configured to control the distance sensor to obtain a distance measurement related to the dimension of the blood vessel V.

Moreover, the one or more measurements can be a single measurement or a composite or average of several different measurements. For example, the measurements can be an average of several measurements taken over a period of seconds (e.g., about 0.5 second, about 1 second, about 2 seconds, less than about 5 seconds, etc.) to account for changes in the dimension of the blood vessel V during the cardiac cycle (e.g., to account for differing vessel diameters during systole and diastole). In some embodiments, the obtained measurements can be communicated to and stored in the memory of the controller 104 and/or another component of the system 100.

At block 406, the method 400 includes determining a diameter of the blood vessel V at or near the target site based on the one or more measurements obtained via the measuring element of the neuromodulation catheter 102. For example, as described in detail above, the controller 104 or another component of the system 100 can process the one or more measurements to determine the diameter of the blood vessel V (e.g., based on known properties of the neuromodulation catheter 102). Based on the determined diameter of the blood vessel V, the controller 104 and/or an operator of the system 100 can assess the likely efficacy of performing neuromodulation therapy at the target site by, for example, correlating the diameter to expected results of neuromodulation therapy (e.g., an expected drop in blood pressure at a certain point after a renal denervation procedure). For example, if the diameter of the blood vessel V is smaller than a baseline value, the controller 104 and/or the operator may determine that neuromodulation therapy is more likely to be effective. In some embodiments, the baseline value may be a diameter measurement of a different location (e.g., a different target site) within the same blood vessel V, or a diameter measurement of a different blood vessel within the patient. In certain embodiments, the baseline measurement can be an average vessel size (e.g., for a patient with similar characteristics) or another value not specific to the patient.

In some embodiments, at block 408, the method 400 can include repositioning the neuromodulation catheter 102 to, for example, a different target site within the blood vessel V. For example, in certain embodiments, the measuring element of the neuromodulation catheter 102 can be used to estimate the diameter of the blood vessel V at multiple locations within the blood vessel V (e.g., as the neuromodulation catheter 102 is moved within the vessel V) to determine a smallest diameter section of the blood vessel V. In some embodiments, the estimated diameter can be displayed to an operator of the system 100 (e.g., on the console in real-time or near-real time), and the operator can view the display and maneuver the neuromodulation catheter 102 within the patient in order to identify the smallest diameter section of the blood vessel V.

Figure 5:
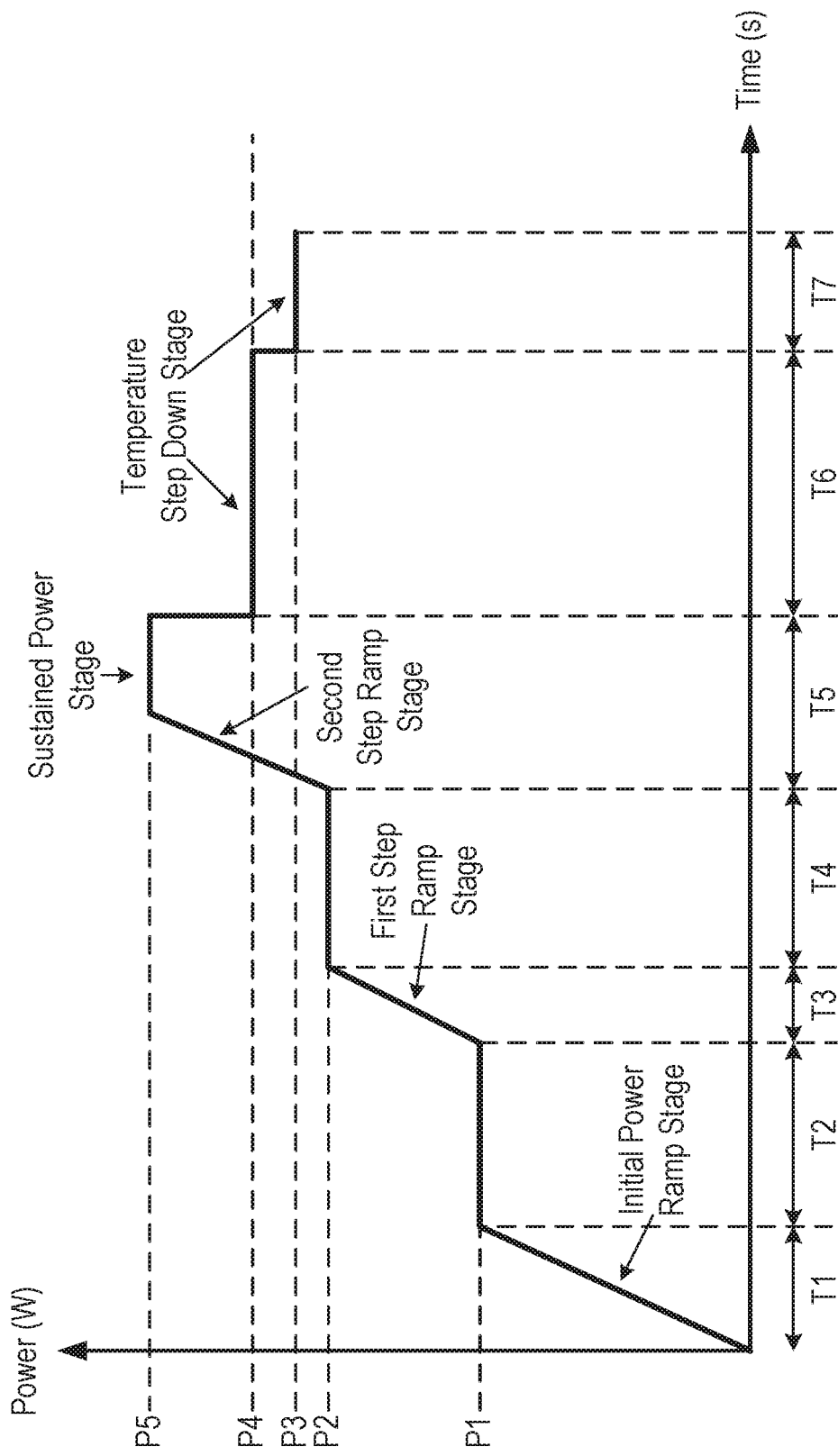
FIG. 5 is a graph illustrating a neuromodulation energy delivery profile in accordance with embodiments of the present technology.

In some embodiments, at block 410, the method 400 can include adjusting one or more parameters of neuromodulation therapy to be delivered at the target site. For example, FIG. 5 is a graph illustrating a suitable neuromodulation energy delivery profile in accordance with embodiments of the present technology. As illustrated in FIG. 5, the neuromodulation therapy may include an initial power ramp stage in which the power of delivered neuromodulation energy is ramped to a power P1 over a time T1. The power P1 can then be sustained for a time T2 before a first step ramp stage in which the power of delivered neuromodulation energy is ramped to a power P2 over a time T3. The power P2 can then be sustained for a time T4 before a second step ramp stage in which the power of delivered neuromodulation energy is ramped to a power P5 over a time T5. The power can then be (i) stepped down to a power P4 and sustained for a time T6 and then (ii) stepped down to a power P3 and sustained for a time T7. In other embodiments, the neuromodulation energy delivery profile may have other configurations and/or parameters.

In some embodiments, the powers P1-P5 and/or the delivery times T1-T7 are standard or baseline values that can be adjusted based on the estimated diameter of the vessel, either manually by an operator of the system 100 and/or automatically by the controller 104. That is, the energy delivery profile can be modified to target renal nerves having a varying depth from the wall of the blood vessel V, as opposed to conventional systems in which an energy delivery profile targets a uniform depth of ablation via a fixed power output (e.g., a fixed maximum sustained power output). For example, in some embodiments, if the diameter of the vessel is measured to be relatively large, the delivery time (e.g., any or all of T1-T7) can be increased and/or the amount of power delivered (e.g., any or all of P1-P5) can be increased to assure that target nerves proximate the target site receive enough neuromodulation energy to be denervated. Accordingly, the present technology can enable a more uniform neuromodulation treatment of targeted renal nerves—regardless of the diameter of the renal vessel.

In certain embodiments, a menu on the console of the system 100 can include two or more selectable options of vessel diameter that each provide a different combination of neuromodulation parameters. In some such embodiments, the options may include, for example, a main vessel option (e.g., for a vessel having a relatively larger diameter) and a branch option (e.g., for a vessel having a relatively smaller diameter). Such an embodiment is based on the assumption that branching vessels have a relatively smaller diameter than a corresponding main vessel. In some embodiments, the menu can include options that are more specific such as, for example, a branch vessel option having more vasculature around it (e.g., increasing heat transfer away from the target site) and a branch vessel option having less vasculature around it. In certain embodiments, the method 400 may determine that no parameters of the neuromodulation energy delivery profile need to be adjusted, and the method 400 can proceed directly to block 412.

Once a suitable target site and parameters of neuromodulation therapy are selected, the method 400 proceeds to block 412 and neuromodulation energy is delivered at the target site in the blood vessel V to ablate nerves proximate to the wall of the blood vessel V. For example, the method 400 can include applying RF energy (e.g., via the electrodes 110), pulsed electrical energy, microwave energy, optical energy, ultrasound energy (e.g., intravascularly delivered ultrasound and/or HIFU), direct heat energy, radiation, cryogenic cooling, chemical-based treatment, and/or another suitable type of neuromodulation energy.

As described above, research suggests that there is a strong correlation between the diameter of a renal blood vessel where neuromodulation therapy is performed and the ultimate efficacy of the neuromodulation procedure (e.g., an ultimate drop in blood pressure). Accordingly, determining the diameter of the renal blood vessel prior to delivering neuromodulation energy and subsequently adjusting the position of a neuromodulation catheter and/or the parameters of neuromodulation energy to be delivered is expected to increase the efficacy of neuromodulation procedures. Accordingly, the system 100 can facilitate efficient and effective neuromodulation treatments.

IV. SELECTED EXAMPLES OF NEUROMODULATION DEVICES AND RELATED SYSTEMS

Figure 6:
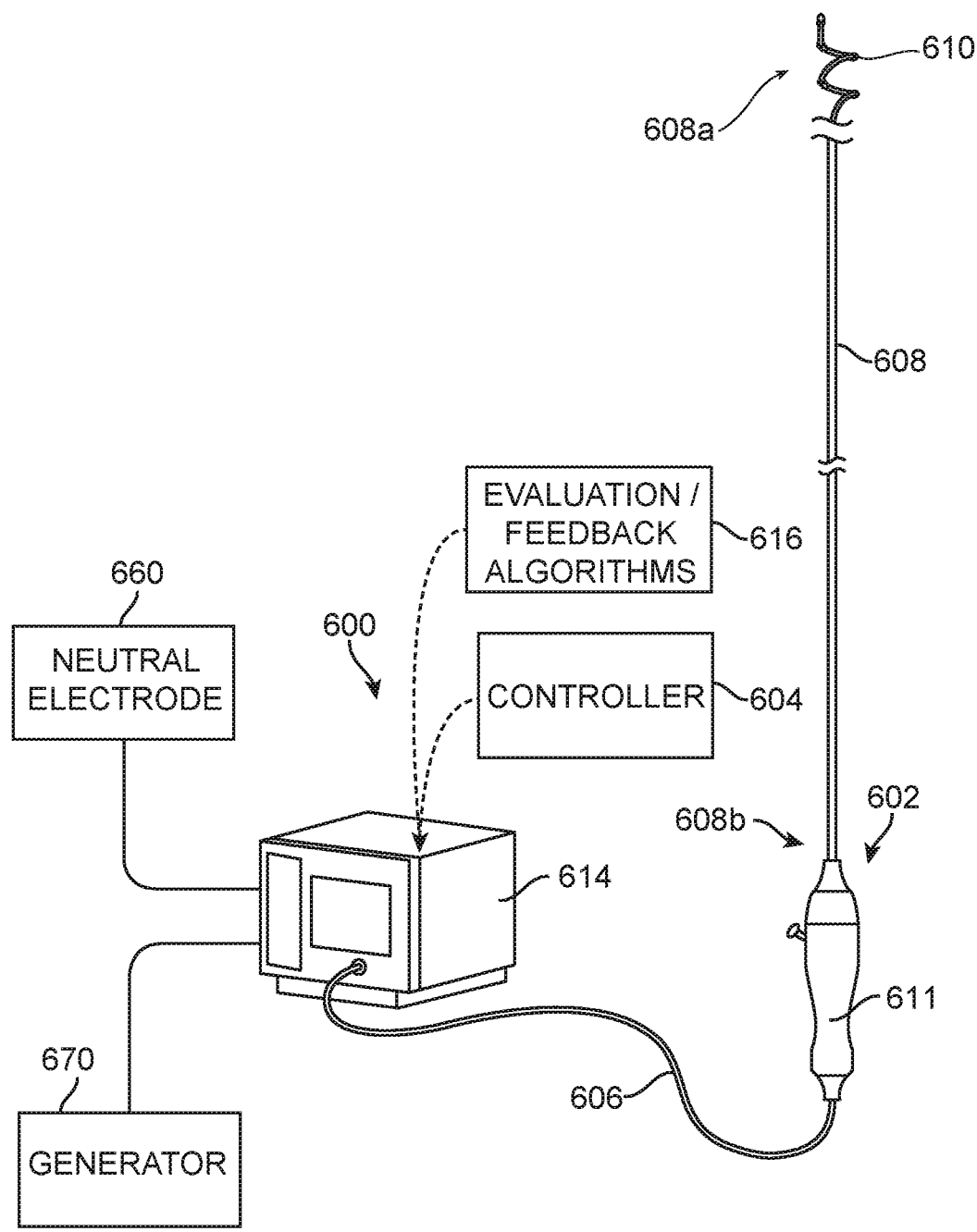
FIG. 6 is a partially schematic illustration of a neuromodulation system configured in accordance with another embodiment of the present technology.

FIG. 6 is a partially schematic illustration of a therapeutic system 600 ("system 600") configured in accordance with an embodiment of the present technology. The system 600 can include various features similar to the neuromodulation system 100 described above with reference to FIGS. 1A-3. In addition, the system 600 can be used to implement any of the methods described herein. As shown in FIG. 6, the system 600 includes a neuromodulation catheter 602, a console 614, and a cable 606 extending therebetween. The neuromodulation catheter 602 can include an elongated shaft 608 having a proximal portion 608b, a distal portion 608a, and a handle 611 operably connected to the elongated shaft 608 at the proximal portion 608b. The elongated shaft 608 can be 2, 3, 4, 5, 6, or 7 French or another suitable size. As shown in FIG. 6, one or more electrodes 610 can be spaced along the distal portion 608a of the elongated shaft 608. The electrodes 610 can be configured to apply electrical stimuli (e.g., radio frequency (RF) energy) to target sites at or proximate to vessels within a patient, temporarily stun nerves, deliver neuromodulation energy to target sites, and/or detect vessel impedance. In various embodiments, certain electrodes 610 can be dedicated to applying stimuli and/or detecting impedance, and the neuromodulation catheter 602 can include other types of therapeutic elements that provide neuromodulation therapy using various modalities, such cryotherapeutic cooling, ultrasound energy, etc.

The console 614 can be configured to control, monitor, supply, and/or otherwise support operation of the neuromodulation catheter 602. In addition, the console 614 can be configured to provide feedback to an operator before, during, and/or after a treatment procedure via an evaluation/feedback algorithm 616. The console 614 can further be configured to generate a selected form and/or magnitude of energy for delivery to tissue at the treatment site via the electrodes 610, and therefore the console 614 may have different configurations depending on the treatment modality of the neuromodulation catheter 602. For example, when the neuromodulation catheter 602 is configured for electrode-based, heat-element-based, or transducer-based treatment, the console 614 can include an energy generator 670 (shown schematically) configured to generate RF energy (e.g., monopolar and/or bipolar RF energy), pulsed energy, microwave energy, optical energy, ultrasound energy (e.g., intravascularly delivered ultrasound and/or high-intensity focused ultrasound (HIFU)), direct heat energy, radiation (e.g., infrared, visible, and/or gamma radiation), and/or another suitable type of energy. In this configuration, the console 614 can also include evaluation/feedback algorithms 616 for controlling the electrodes 610. In selected embodiments, the energy generator 670 can be configured to deliver a monopolar electric field via one or more of the electrodes 610. In such embodiments, a neutral or dispersive electrode 660 may be electrically coupled to the energy generator 670 and attached to the exterior of the patient. When the neuromodulation catheter 602 is configured for cryotherapeutic treatment, the console 614 can include a refrigerant reservoir (not shown) and can be configured to supply the neuromodulation catheter 602 with refrigerant. Similarly, when the neuromodulation catheter 602 is configured for chemical-based treatment (e.g., drug infusion), the console 614 can include a chemical reservoir (not shown) and can be configured to supply the neuromodulation catheter 602 with one or more chemicals.

In various embodiments, the system 600 can further include a controller 604 communicatively coupled to the neuromodulation catheter 602. The controller 604 can be configured to initiate, terminate, and/or adjust operation of one or more components (e.g., the electrodes 610) of the neuromodulation catheter 602 directly and/or via the console 614 and/or via a wired or wireless communication link. In various embodiments, the system 600 can include multiple controllers. In other embodiments, the neuromodulation catheter 602 can be communicatively coupled to a single controller 604. The controller(s) 604 can be integrated with the console 614 or the handle 611 positioned outside the patient and used to operate the system 600. In other embodiments, the controller 604 can be omitted or have other suitable locations (e.g., within the handle 611, along the cable 606, etc.). The controller 604 can include computer-implemented instructions to initiate, terminate, and/or adjust operation of one or more components of the neuromodulation catheter 602 directly and/or via another aspect of the system (e.g., the console 614 and/or handle 611). For example, the controller 604 can further provide instructions to the neuromodulation catheter 602 to apply neuromodulatory energy to the treatment site (e.g., RF energy via the electrodes 610). The controller 604 can be configured to execute an automated control algorithm and/or to receive control instructions from an operator. Further, the controller 604 can include or be linked to the evaluation/feedback algorithm 616 that can provide feedback to an operator before, during, and/or after a treatment procedure via a console, monitor, and/or other user interface.

Figure 7:
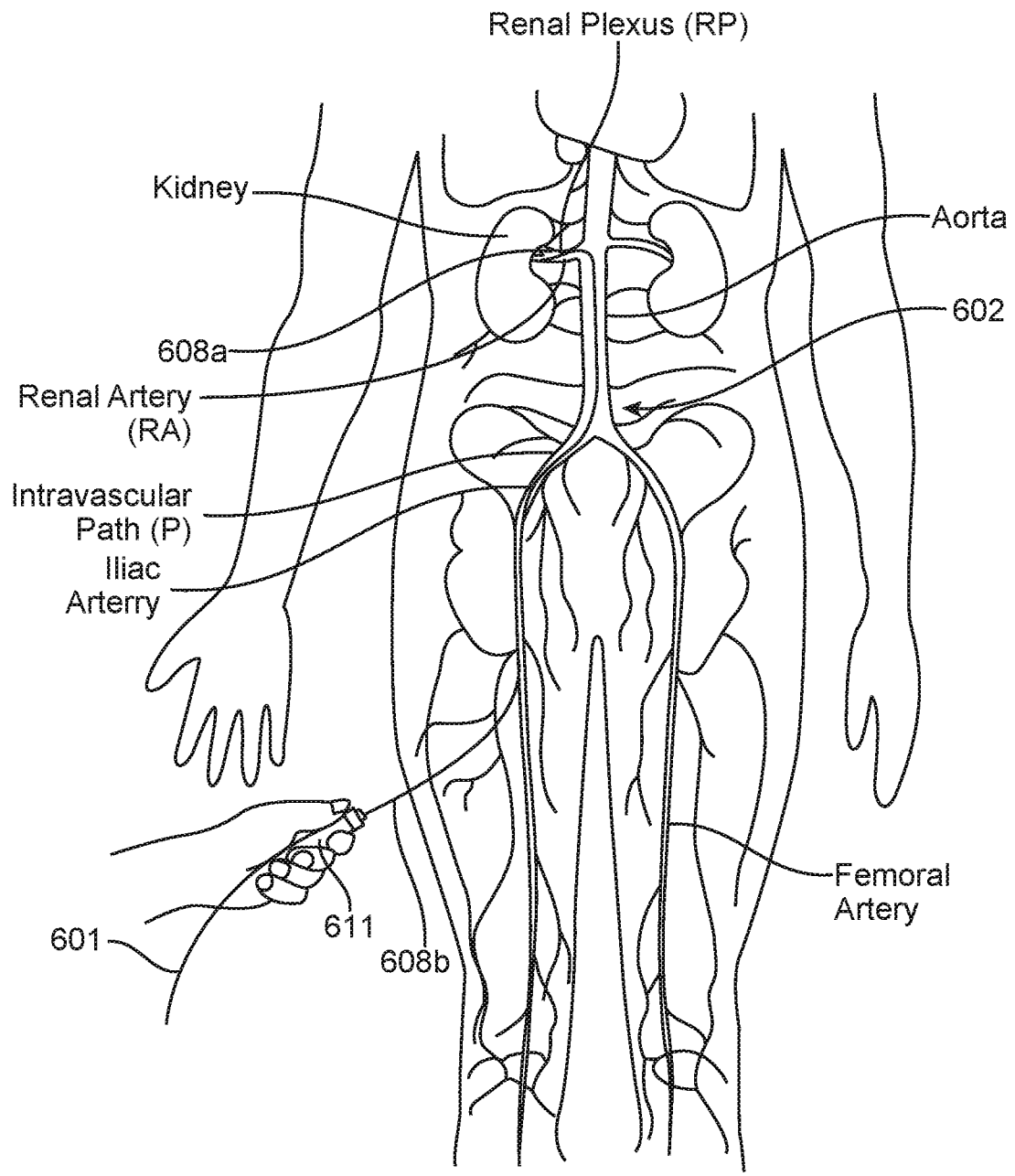
FIG. 7 illustrates modulating renal nerves and/or evaluating the neuromodulation therapy with the system of FIG. 6 in accordance with an embodiment of the present technology.

FIG. 7 (with additional reference to FIG. 6) illustrates modulating renal nerves in accordance with an embodiment of the system 600. The neuromodulation catheter 602 provides access to the renal plexus RP through an intravascular path P, such as a percutaneous access site in the femoral (illustrated), brachial, radial, or axillary artery to a targeted treatment site within a respective renal artery RA. By manipulating the proximal portion 608b of the elongated shaft 608 from outside the intravascular path P, a clinician may advance the elongated shaft 608 through the sometimes tortuous intravascular path P and remotely manipulate the distal portion 608a of the elongated shaft 608. In the embodiment illustrated in FIG. 7, the distal portion 608a of the elongated shaft 608 is delivered intravascularly to the treatment site using a guidewire 601 in an OTW technique. The distal end of the neuromodulation catheter 602 may define a passageway for receiving the guidewire 601 for delivery of the neuromodulation catheter 602 using either OTW or RX techniques. At the treatment site, the guidewire 601 can be at least partially withdrawn or removed, and the distal portion of the neuromodulation catheter 602 can transform or otherwise be moved to a deployed arrangement for recording neural activity and/or delivering energy at the treatment site. In other embodiments, the neuromodulation catheter 602 may be delivered to the treatment site within a guide sheath (not shown) with or without using the guidewire 601. When the neuromodulation catheter 602 is at the target site, the guide sheath may be at least partially withdrawn or retracted and the distal portion of the neuromodulation catheter 602 can be transformed into the deployed arrangement. In still other embodiments, the elongated shaft 608 may be steerable itself such that the neuromodulation catheter 602 may be delivered to the treatment site without the aid of the guidewire 601 and/or guide sheath.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the neuromodulation catheter 602. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the neuromodulation catheter 602. Further, in some embodiments, image guidance components (e.g., IVUS, OCT) may be integrated with the neuromodulation catheter 602 and/or run in parallel with the neuromodulation catheter 602 to provide image guidance during positioning of the neuromodulation catheter 602. For example, image guidance components (e.g., IVUS or OCT) can be coupled to the neuromodulation catheter 602 to provide three-dimensional images of the vasculature proximate the target site to facilitate positioning or deploying the multi-electrode assembly within the target renal blood vessel.

Energy from the electrodes 610 (FIG. 6) and/or other energy delivery elements may then be applied to target tissue to induce one or more desired neuromodulating effects on localized regions of the renal artery RA and adjacent regions of the renal plexus RP, which lay intimately within, adjacent to, or in close proximity to the adventitia of the renal artery RA. The purposeful application of the energy may achieve neuromodulation along all or at least a portion of the renal plexus RP. The neuromodulating effects are generally a function of, at least in part, power, time, contact between the energy delivery elements and the vessel wall, and blood flow through the vessel. The neuromodulating effects may include denervation, thermal ablation, and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

V. RENAL NEUROMODULATION

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic over activity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable treatment sites during a treatment procedure. The treatment site can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery.

Renal neuromodulation can include a cryotherapeutic treatment modality alone or in combination with another treatment modality. Cryotherapeutic treatment can include cooling tissue at a treatment site in a manner that modulates neural function. For example, sufficiently cooling at least a portion of a sympathetic renal nerve can slow or potentially block conduction of neural signals to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Neuromodulation using a cryotherapeutic treatment in accordance with embodiments of the present technology can include cooling a structure proximate an inner surface of a body lumen wall such that tissue is effectively cooled to a depth where sympathetic renal nerves reside. For example, in some embodiments, a cooling assembly of a cryotherapeutic device can be cooled to the extent that it causes therapeutically-effective, cryogenic renal neuromodulation. In other embodiments, a cryotherapeutic treatment modality can include cooling that is not configured to cause neuromodulation. For example, the cooling can be at or above cryogenic temperatures and can be used to control neuromodulation via another treatment modality (e.g., to protect tissue from neuromodulating energy).

Renal neuromodulation can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, neuromodulation in accordance with embodiments of the present technology can include delivering RF energy, pulsed energy, microwave energy, optical energy, focused ultrasound energy (e.g., HIFU energy), or another suitable type of energy alone or in combination. An electrode or transducer used to deliver this energy can be used alone or with other electrodes or transducers in a multi-electrode or multi-transducer array. Furthermore, the energy can be applied from within the body (e.g., within the vasculature or other body lumens in a catheter-based approach) and/or from outside the body (e.g., via an applicator positioned outside the body). Furthermore, energy can be used to reduce damage to non-targeted tissue when targeted tissue adjacent to the non-targeted tissue is subjected to neuromodulating cooling.

Neuromodulation using focused ultrasound energy (e.g., HIFU energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, optical coherence tomography, or another suitable imaging modality). For example, imaging can be used to identify an anatomical position of a treatment location (e.g., as a set of coordinates relative to a reference point). The coordinates can then entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight).

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of vascular or luminal structures that perfuse the target neural fibers. In cases where vascular structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C. (e.g., less than about 85° C., less than about 80° C., or less than about 75° C.).

Renal neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. The chemical, for example, can be guanethidine, ethanol, phenol, a neurotoxin, or another suitable agent selected to alter, damage, or disrupt nerves. A variety of suitable techniques can be used to deliver chemicals to tissue at a treatment location. For example, chemicals can be delivered via one or more needles originating outside the body or within the vasculature or other body lumens. In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a body lumen wall, electrophoresis, or another suitable mechanism. Similar techniques can be used to introduce chemicals that are not configured to cause neuromodulation, but rather to facilitate neuromodulation via another treatment modality.

VI. RELATED ANATOMY AND PHYSIOLOGY

As noted previously, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

A. The Sympathetic Chain

Figure 8:
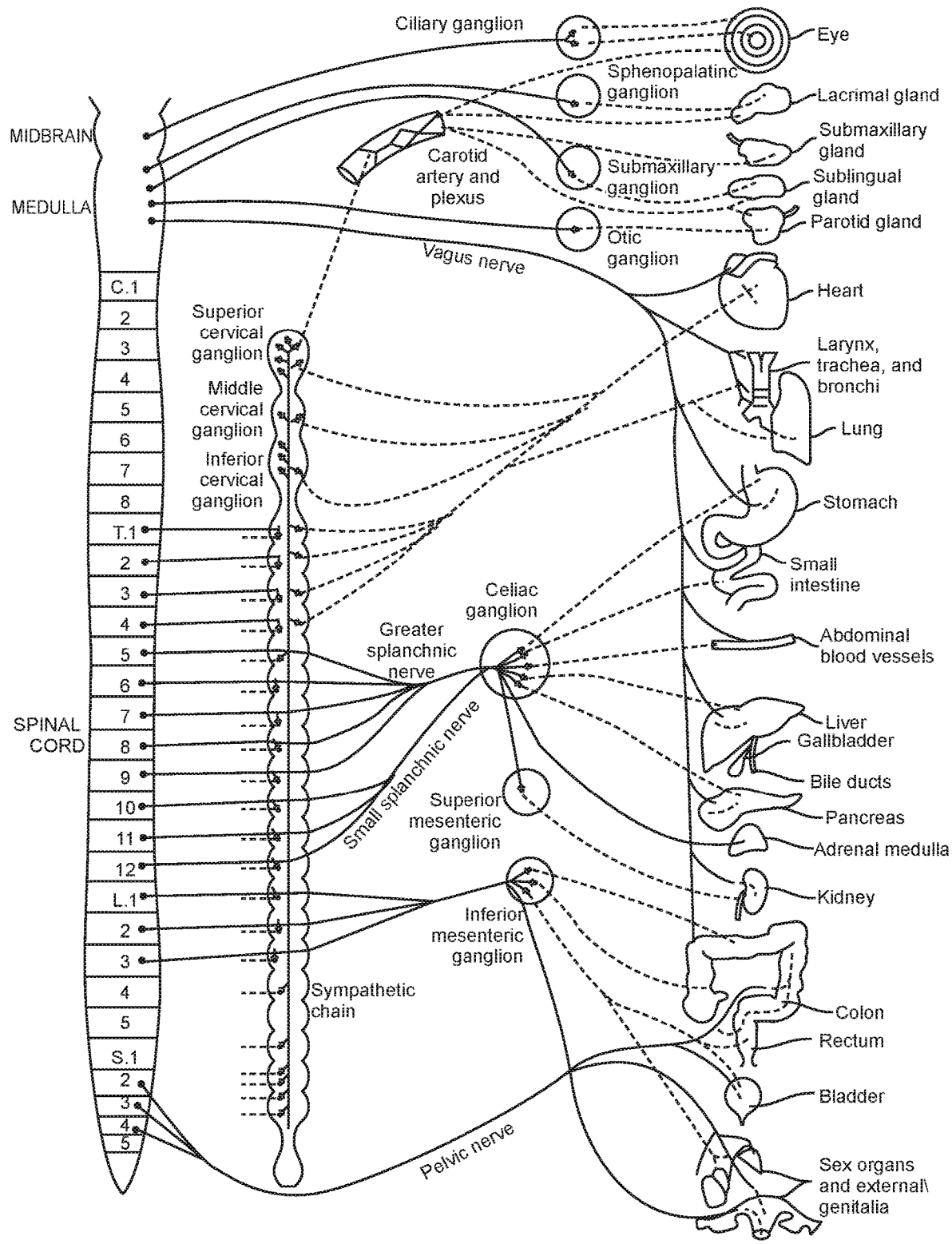
FIG. 8 is a conceptual illustration of the sympathetic nervous system (SNS) and how the brain communicates with the body via the SNS.

As shown in FIG. 8, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

1. Innervation of the Kidneys

Figure 9:
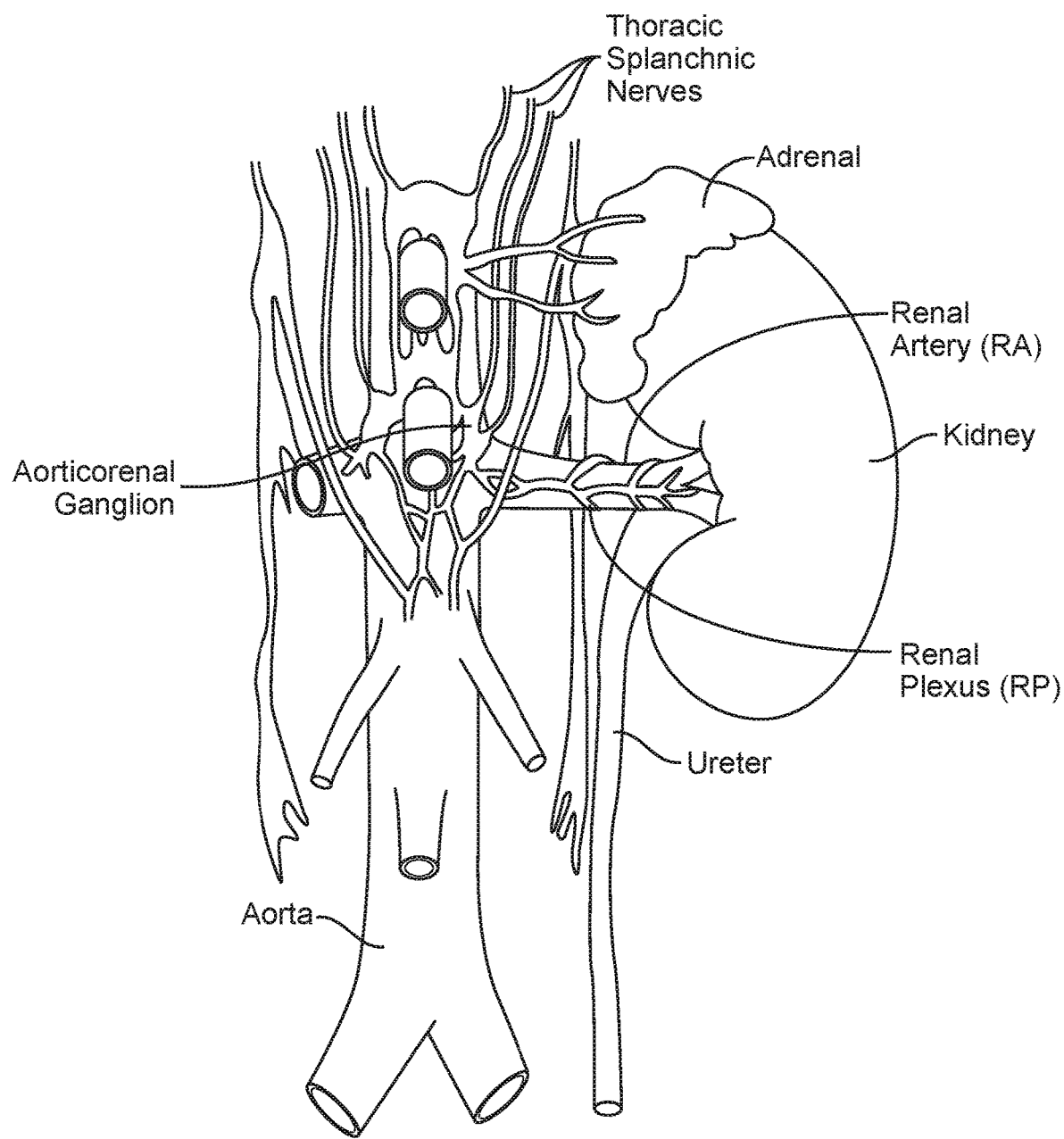
FIG. 9 is an enlarged anatomic view of nerves innervating a left kidney to form the renal plexus surrounding the left renal artery.

As FIG. 9 shows, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

2. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well-known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 10:
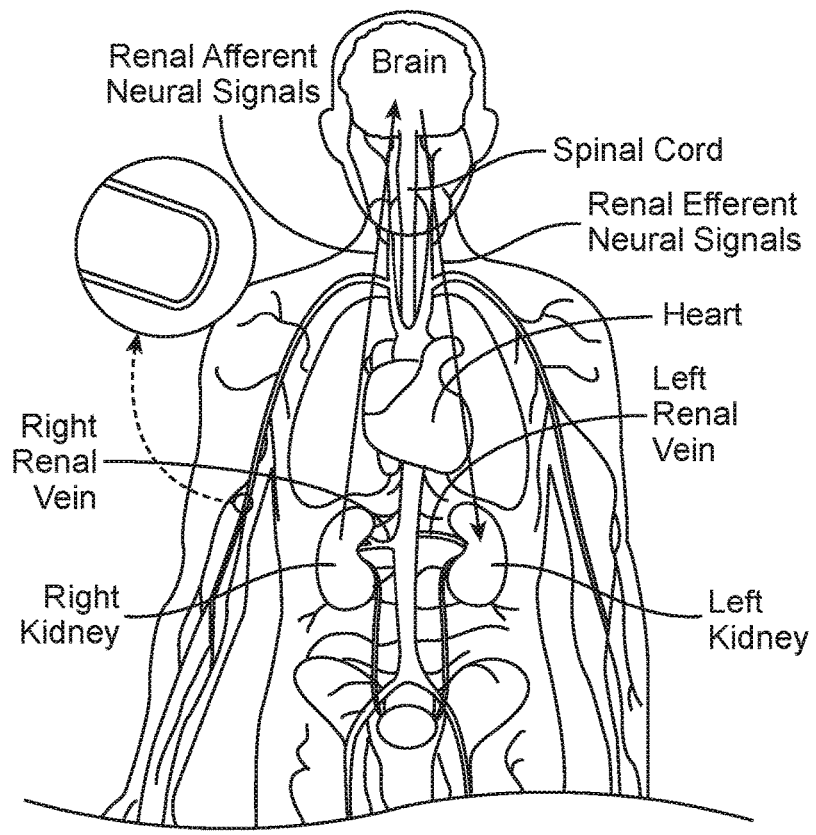
FIGS. 10 and 11 are anatomic and conceptual views, respectively, of a human body depicting neural efferent and afferent communication between the brain and kidneys.
Figure 11:
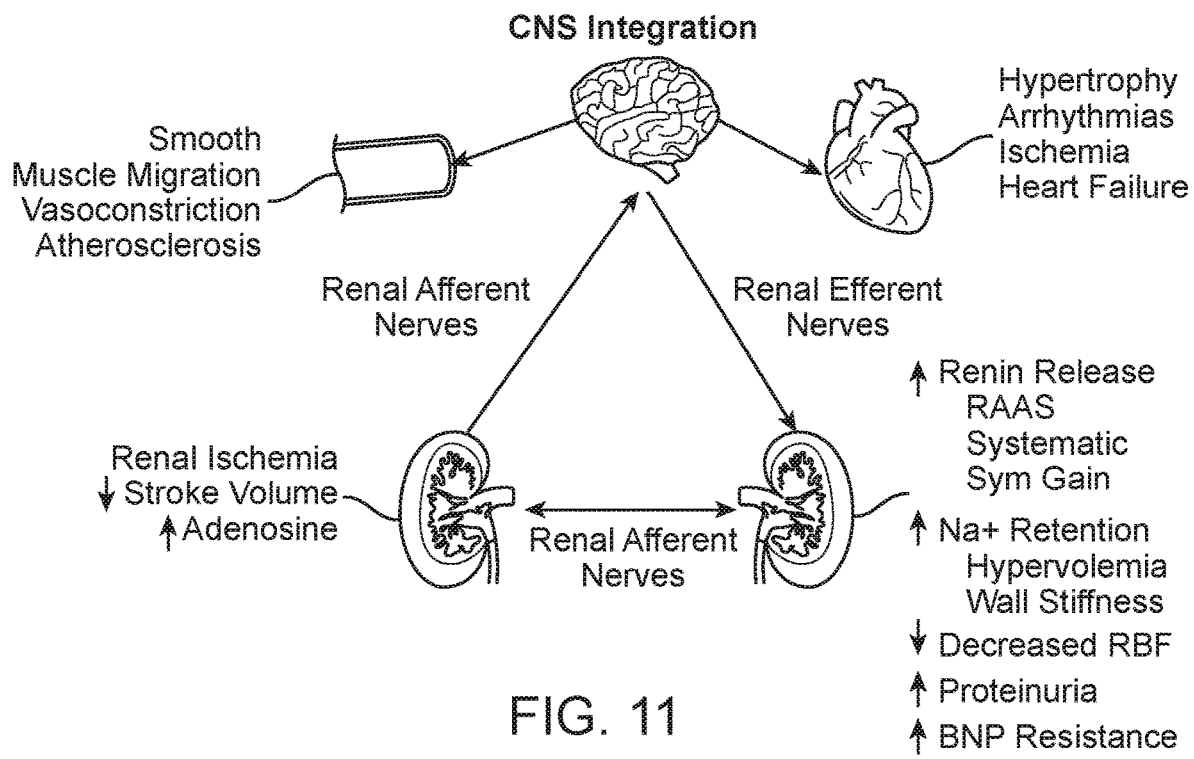

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 10 and 11, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 8. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 12:
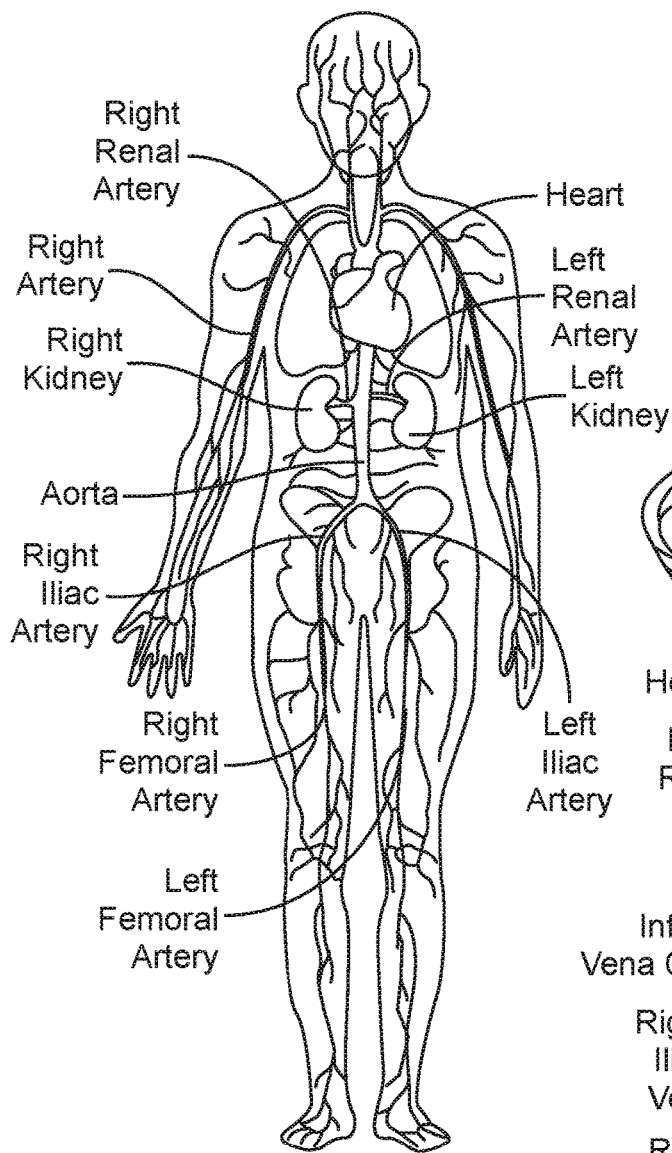
FIGS. 12 and 13 are anatomic views of the arterial vasculature and venous vasculature, respectively, of a human.

In accordance with the present technology, neuromodulation of a left and/or right renal plexus (RP), which is intimately associated with a left and/or right renal artery, may be achieved through intravascular access. As FIG. 12 shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 13:
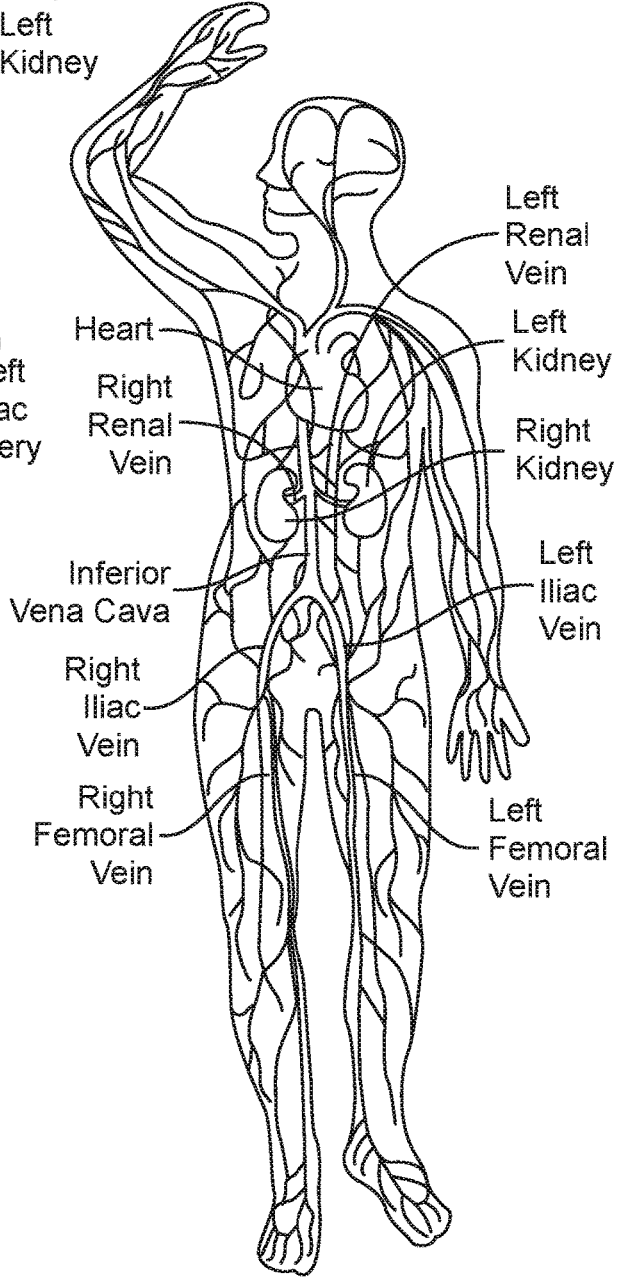

As FIG. 13 shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. For example, navigation can be impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the energy delivery element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

VII. EXAMPLES

1. A system, comprising:
    a neuromodulation catheter including—
        an elongated shaft having a distal portion configured to be intravascularly positioned at a target site within a renal blood vessel of a human patient; and
        a plurality of electrodes spaced apart along the distal portion of the shaft, the plurality of electrodes including a first electrode and a second electrode, wherein the electrodes are configured to deliver neuromodulation energy to target renal nerves at or adjacent the target site; and
    a controller configured to be communicatively coupled to the electrodes, wherein the controller is further configured to—
        obtain an impedance measurement between the first and second electrodes; and
        based on the impedance measurement, determine a diameter of the renal blood vessel at or near the target site.

2. The system of example 1, further comprising an energy generator external to the patient and coupled to the plurality of electrodes and the controller, wherein the controller is configured to cause the energy generator to deliver neuromodulation energy via the first and second electrodes based on the determined diameter of the renal blood vessel.

3. The system of example 2 wherein the controller is further configured to—
    if the diameter of the renal blood vessel is a first value, deliver neuromodulation energy having a first set of parameters; and
    if the diameter of the renal blood vessel is a second value different than the first value, deliver neuromodulation energy having a second set of parameters,
    wherein at least one parameter in the second set of parameters is different from a corresponding parameter in the first set of parameters.

4. The system of example 3 wherein the at least one parameter is an amount of neuromodulation energy.

5. The system of example 3 wherein the at least one parameter is a delivery time of the neuromodulation energy.

6. The system of any one of examples 1-5 wherein the impedance measurement is an average measurement over a period of less than about 5 seconds.

7. A system, comprising:
    a neuromodulation catheter including—
        an elongated shaft having a distal portion configured to be intravascularly positioned at a target site within a blood vessel of a human patient,
        wherein the distal portion is transformable between a low-profile delivery arrangement and an expanded treatment arrangement at the target site within the blood vessel;
        a plurality of electrodes spaced apart along the distal portion of the shaft, wherein, when the distal portion is in the expanded treatment arrangement, the plurality of electrodes are positioned in apposition with an inner wall of the blood vessel and configured to deliver neuromodulation energy to target nerves at or adjacent the target site; and
        a distance sensor at the distal portion of the elongated shaft and configured to detect a distance measurement corresponding to a distance between a first portion of the elongated shaft and a second portion of the elongated shaft; and
    a controller configured to be communicatively coupled to the distance sensor, wherein the controller is further configured to—
        obtain the distance measurement from the distance sensor; and
        based on the distance measurement, determine a diameter of the blood vessel at or near the target site.

8. The system of example 7, further comprising an energy generator external to the patient and operably coupled to the electrodes and the controller, wherein the controller is configured to— if the diameter of the blood vessel is a first value, instruct the energy generator to deliver neuromodulation energy having a first set of parameters via the electrodes; and if the diameter of the blood vessel is a second value, instruct the energy generator to deliver neuromodulation energy having a second set of parameters via the electrodes, wherein at least one parameter in the first set of parameters is different than a corresponding parameter in the second set of parameters.

9. The system of example 8 wherein the at least one parameter is an amount of neuromodulation energy and a delivery time of the neuromodulation energy.

10. The system of any one of examples 7-9 wherein determining the diameter of the blood vessel is based at least in part on a known dimension of the neuromodulation catheter.

11. A method, comprising:
positioning a neuromodulation catheter having one or more electrodes at a target site within a renal blood vessel of a human patient;
obtaining a measurement related to a diameter of the renal blood vessel via the neuromodulation catheter; and
based on the measurement, determining a diameter of the renal blood vessel at or near the target site.

12. The method of example 11, further comprising, based on the diameter of the renal blood vessel, adjusting a parameter of neuromodulation energy to be delivered to the renal blood vessel at the target site.

13. The method of example 12, further comprising delivering the neuromodulation energy to renal nerves at the target site via the one or more electrodes of the neuromodulation catheter.

14. The method of example 12 or example 13 wherein the parameter of neuromodulation energy is at least one of an amount of neuromodulation energy and a delivery time of neuromodulation energy.

15. The method of any one of examples 11-14, further comprising:
comparing the determined diameter of the renal blood vessel to a baseline value; and
based on the comparison, assessing the likely efficacy of neuromodulation energy to be delivered to the renal blood vessel at the target site.

16. The method of any one of examples 11-15, further comprising:
comparing the determined diameter of the renal blood vessel to a baseline value; and
when the determined diameter is greater than the baseline value, repositioning the neuromodulation catheter to a different target site within the renal blood vessel.

17. The method of any one of examples 11-16 wherein obtaining the measurement related to the dimension of the renal blood vessel includes detecting an impedance between at least two of the one or more electrodes of the neuromodulation catheter.

18. The method of any one of examples 11-16 wherein obtaining the measurement related to the dimension of the renal blood vessel includes detecting an impedance between each pair of the one or more electrodes of the neuromodulation catheter.

19. The method of any one of examples 11-16 wherein obtaining the measurement related to the dimension of the renal blood vessel includes detecting a distance measurement corresponding to a distance between a first portion and a second portion of the neuromodulation catheter.

20. The method of any one of examples 11-16 wherein obtaining the measurement related to the dimension of the renal blood vessel includes—
inflating a balloon coupled to the neuromodulation catheter; and
determining when the balloon contacts an inner wall of the renal blood vessel.

VIII. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system for performing neuromodulation therapy to target one or more nerves of a patient, the system comprising:
   a neuromodulation catheter including:
      an elongated shaft having a distal portion configured to be intravascularly positioned at a target site within a blood vessel of the patient; and
      a plurality of electrodes spaced apart along the distal portion of the shaft, the plurality of electrodes including a first electrode and a second electrode, wherein the plurality of electrodes are configured to deliver neuromodulation energy to target the one or more nerves at or adjacent the target site;
   an energy generator; and
   a controller configured to:
      obtain a plurality of impedance measurements between the first and second electrodes at a location within the blood vessel over a period of time, wherein the location is at the target site;
      based on the plurality of impedance measurements, determine a pre-neuromodulation diameter of the blood vessel at the location;
      determine at least one parameter of initial neuromodulation energy based on the pre-neuromodulation diameter of the blood vessel; and
      cause the energy generator to deliver of the initial neuromodulation energy to the one or more nerves based on the at least one parameter.

2. The system of claim 1, wherein the energy generator is external to the patient and is coupled to the plurality of electrodes, and wherein the controller is configured to cause the energy generator to deliver the initial neuromodulation energy by at least causing the energy generator to deliver the initial neuromodulation energy via the first and second electrodes based on the determined pre-neuromodulation diameter of the blood vessel.

3. The system of claim 2, wherein the controller is further configured to:
   cause the energy generator to deliver the initial neuromodulation energy with a first set of parameters if the pre-neuromodulation diameter of the blood vessel is a first value; and
   cause the energy generator to deliver the initial neuromodulation energy with a second set of parameters if the pre-neuromodulation diameter of the blood vessel is a second value different than the first value, wherein at least one parameter in the second set of parameters is different from a corresponding parameter in the first set of parameters.

4. The system of claim 3, wherein the at least one parameter in the second set of parameters is an amount of the initial neuromodulation energy or a delivery time of the initial neuromodulation energy.

5. The system of claim 1, wherein the controller is configured to determine the pre-neuromodulation diameter of the blood vessel based on the plurality of impedance measurements by at least determining an average measurement of the plurality of impedance measurements.

6. The system of claim 1, wherein the period of time is selected to account for changes in a dimension of the blood vessel during a cardiac cycle.

7. The system of claim 1, wherein to cause the energy generator to deliver the initial neuromodulation energy to the one or more nerves based on the at least one parameter, the controller is configured to communicate the at least one parameter of the initial neuromodulation energy to the energy generator, wherein the energy generator is configured to deliver the initial neuromodulation therapy to the one or more nerves based on the at least one parameter.

8. A system for performing neuromodulation therapy to target one or more nerves of a patient, the system comprising:
   a neuromodulation catheter including:
      an elongated shaft having a distal portion configured to be intravascularly positioned at a target site within a blood vessel of the patient,
      wherein the distal portion is transformable between a low-profile delivery arrangement and an expanded treatment arrangement at the target site within the blood vessel;
      a plurality of electrodes spaced apart along the distal portion of the shaft, wherein, when the distal portion is in the expanded treatment arrangement, the plurality of electrodes are configured to be positioned in apposition with an inner wall of the blood vessel and configured to deliver neuromodulation energy to the one or more nerves at or adjacent the target site; and
      a distance sensor at the distal portion of the elongated shaft and configured to generate an output indicative of a distance between a first portion of the elongated shaft and a second portion of the elongated shaft;
   an energy generator; and
   a controller configured to be communicatively coupled to the distance sensor, wherein the controller is further configured to:
      determine a distance measurement based on the output from the distance sensor;
      based on the distance measurement, determine a pre-neuromodulation diameter of the blood vessel at or near the target site;
      determine at least one parameter of initial neuromodulation energy based on the pre-neuromodulation diameter of the blood vessel; and
      cause the energy generator to deliver the initial neuromodulation energy to the one or more nerves based on the at least one parameter.

9. The system of claim 8, wherein the energy generator is external to the patient and is operably coupled to the plurality of electrodes and the controller, wherein the controller is configured to cause the energy generator to deliver the initial neuromodulation energy by at least:
   instructing the energy generator to deliver the initial neuromodulation energy with a first set of parameters via the plurality of electrodes if the pre-neuromodulation diameter of the blood vessel is a first value; and
   instructing the energy generator to deliver the initial neuromodulation energy with a second set of parameters via the plurality of electrodes if the pre-neuromodulation diameter of the blood vessel is a second value, the second value being different from the first value,
   wherein at least one parameter in the first set of parameters is different than a corresponding parameter in the second set of parameters.

10. The system of claim 9, wherein the at least one parameter in the first set of parameters is an amount of the initial neuromodulation energy and a delivery time of the initial neuromodulation energy.

11. The system of claim 8, wherein the controller is configured to determine the pre-neuromodulation diameter of the blood vessel based at least in part on a known dimension of the neuromodulation catheter.

12. A method comprising:
obtaining a plurality of impedance measurements at a location within a blood vessel of a patient via a neuromodulation catheter over a period of time, wherein the neuromodulation catheter is positioned in the blood vessel and comprises one or more electrodes, and wherein the location is at a target site;
based on the plurality of impedance measurements, determining a pre-neuromodulation diameter of the blood vessel at the location;
determining at least one parameter of initial neuromodulation energy based on the pre-neuromodulation diameter of the blood vessel; and
causing an energy generator to deliver the initial neuromodulation energy to one or more nerves at or around the location based on the at least one parameter.

13. The method of claim 12, further comprising selecting the location for the delivery of the initial neuromodulation therapy based on the pre-neuromodulation diameter of the blood vessel at the location.

14. The method of claim 13, further comprising determining the pre-neuromodulation diameter of the blood vessel at each location of a plurality of different locations along the blood vessel by at least:
obtaining a respective plurality of impedance measurements related to the diameter of the blood vessel at the respective location of the plurality of different locations; and
determining the pre-neuromodulation diameter of the blood vessel at each location of the plurality of different locations based on the respective plurality of impedance measurements,
wherein selecting the location comprises selecting the location with a smallest pre-neuromodulation diameter of the blood vessel from the plurality of different locations.

15. The method of claim 12, wherein the at least one parameter of initial neuromodulation energy comprises at least one of an amount of the initial neuromodulation energy based on the determining or a delivery time of the initial neuromodulation energy.

16. The method of claim 12, further comprising:
comparing the pre-neuromodulation diameter of the blood vessel at the location to a baseline value; and
based on the comparison, assessing the likely efficacy of the initial neuromodulation energy to be delivered to the blood vessel at the target site.

17. The method of claim 12, wherein the location comprises a first location, and wherein the method further comprises:
comparing the pre-neuromodulation diameter of the blood vessel at the first location to a baseline value;
determining the pre-neuromodulation diameter at the first location is greater than the baseline value based on the comparing; and
repositioning the neuromodulation catheter from the first location to a second location within the blood vessel based on determining that the pre-neuromodulation diameter at the first location is greater than the baseline value.

18. The method of claim 12, wherein obtaining the plurality of impedance measurements includes detecting an impedance between at least two of the one or more electrodes of the neuromodulation catheter.

19. The method of claim 12, wherein obtaining the plurality of impedance measurements includes detecting an impedance between each pair of the one or more electrodes of the neuromodulation catheter.

20. The method of claim 12, wherein obtaining the plurality of impedance measurements includes determining a distance measurement corresponding to a distance between a first portion and a second portion of the neuromodulation catheter.

21. The method of claim 12, wherein obtaining the plurality of impedance measurements includes:
inflating a balloon coupled to the neuromodulation catheter; and
determining when the balloon contacts an inner wall of the blood vessel.

22. The method of claim 12, wherein causing the energy generator to deliver the initial neuromodulation energy to the one or more nerves based on the at least one parameter comprises:
communicating the at least one parameter of the initial neuromodulation energy to the energy generator, wherein the energy generator is configured to deliver the initial neuromodulation therapy to the one or more nerves based on the at least one parameter.

* * * * *